US012282020B2

(12) United States Patent
Bund et al.

(10) Patent No.: US 12,282,020 B2
(45) Date of Patent: Apr. 22, 2025

(54) USE OF BMMFI Rep PROTEIN AS BIOMARKER FOR COLORECTAL CANCER

(71) Applicant: DEUTSCHES KREBSFORSCHUNGSZENTRUM STIFTUNG DES ÖFFENTLICHEN RECHTS, Heidelberg (DE)

(72) Inventors: Timo Bund, Dossenheim (DE); Harald Zur Hausen, Wald-Michelbach (DE); Ethel-Michele De Villiers-Zur Hausen, Wald-Michelbach (DE); Claudia Tessmer, Schwarzach (DE); Mathias Heikenwalder, Heidelberg (DE); Achim Weber, Zurich (CH); Amelie Burk-Körner, Heidelberg (DE)

(73) Assignee: DEUTSCHES KREBSFORSCHUNGSZENTRUM STIFTUNG DES ÖFFENTLICHEN RECHTS, Heidelberg (DE)

( * ) Notice: Subject to any disclaimer, the term of this patent is extended or adjusted under 35 U.S.C. 154(b) by 1128 days.

(21) Appl. No.: 16/939,154

(22) Filed: Jul. 27, 2020

(65) Prior Publication Data

US 2021/0003575 A1   Jan. 7, 2021

Related U.S. Application Data

(63) Continuation-in-part of application No. PCT/EP2019/051868, filed on Jan. 25, 2019.

(30) Foreign Application Priority Data

Jan. 30, 2018 (EP) ..................................... 18154190

(51) Int. Cl.
*G01N 33/574* (2006.01)
*G01N 33/577* (2006.01)

(52) U.S. Cl.
CPC ..... *G01N 33/57419* (2013.01); *G01N 33/577* (2013.01); *G01N 2333/70503* (2013.01)

(58) Field of Classification Search
CPC ........... G01N 33/57419; G01N 33/577; G01N 2333/70503
See application file for complete search history.

(56) References Cited

FOREIGN PATENT DOCUMENTS

WO   2016/005054 A2   1/2016
WO   2016/005054 A8   1/2016

OTHER PUBLICATIONS

Rattray, et al., Curr Pharmacol Rep. 3(3):114-125. (2017) (Year: 2017).*
Chiu et al., Antibodies, 8(55):1-80. (2019 (Year: 2019).*
Zur Hausen et. al. (Current topics in microbiology and immunology. 407:83-116 (2017) (Year: 2017).*
Zhang et. al. (European Journal of Cancer. 49:3320-3334. (2013)) (Year: 2013).*
Kim Y.C. Fung, et al., Blood-Based Protein Biomarker Panel for the Detection of Colorectal Cancer, PLOS ONE (Mar. 20, 2015) vol. 10, No. 3., p. 1-11. DOI:10.1377/journal.phone.0120425.
Corinna Whitley, et al., Novel Replication-Competent Circular DNA Molecules from Healthy Cattle Serum and Milk and Multiple Sclerosis-Affected Human Brain Tissue, Genome Announcements (Jul./Aug. 2014) vol. 2, Issue 4, p. 1-2.
International Search Report issued Apr. 10, 2019 in PCT/EP2019/051868.
Timo Bund, et al., Analysis of chronic inflammatory lesions of the colon for BMMF Rep antigen expression and CD68 macrophage interactions, PNAS (2021) vol. 118, No. 12, p. 1-9.
Turgay Kilic, et al., Structural analysis of a replication protein encoded by a plasmid isolated from a multiple sclerosis patient, Acta Cryst. (2019) D75, p. 498-504.

* cited by examiner

*Primary Examiner* — Meera Natarajan
*Assistant Examiner* — Francesca Edgingtongiordano
(74) *Attorney, Agent, or Firm* — Duane Morris LLP; Thomas J. Kowalski

(57) ABSTRACT

The present invention relates to the use of BMW Rep-protein as a biomarker for colon cancer.

4 Claims, 16 Drawing Sheets

Specification includes a Sequence Listing.

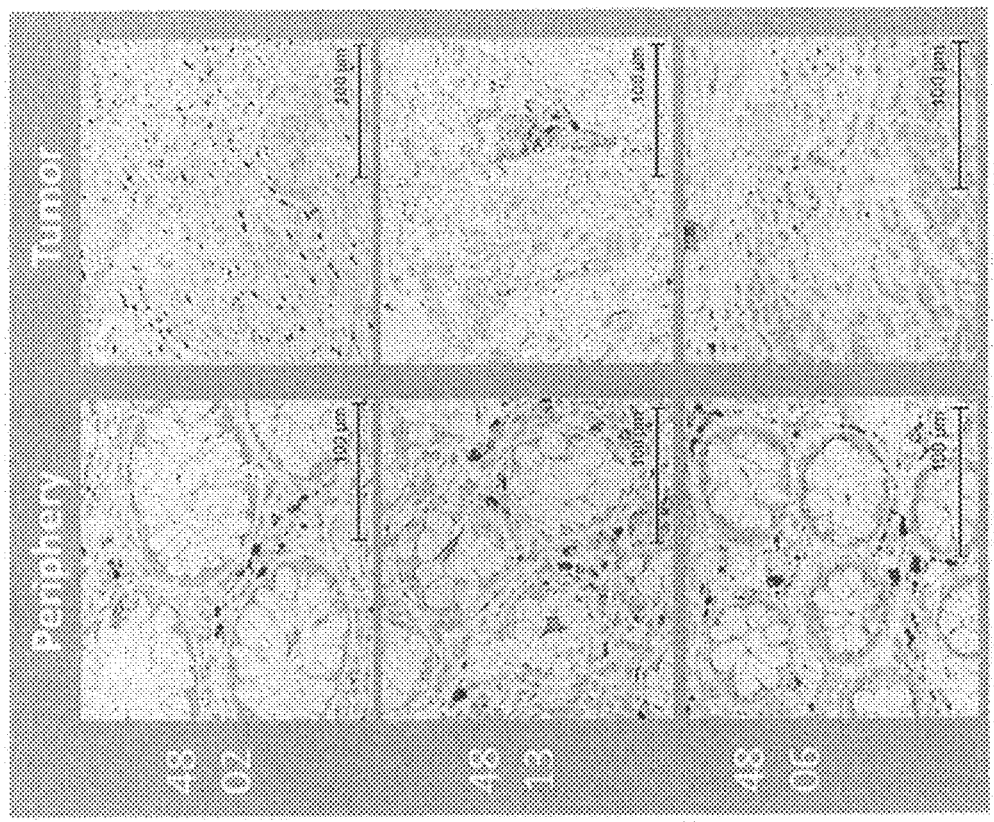
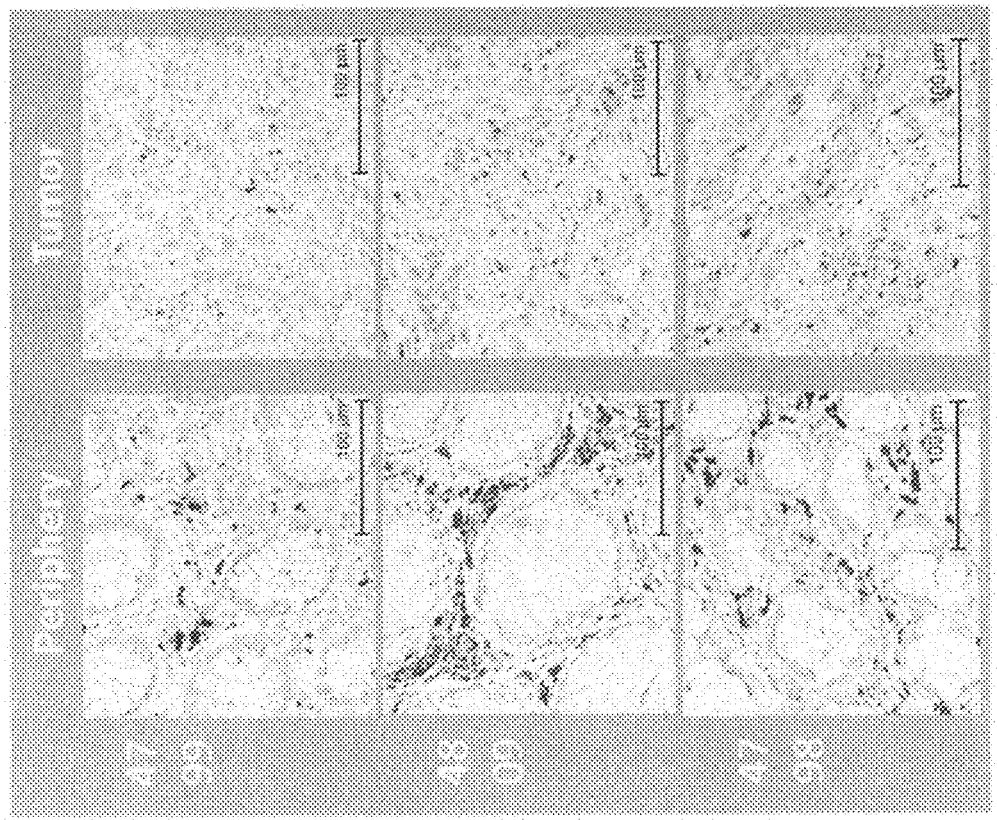
Fig. 4

Fig. 5
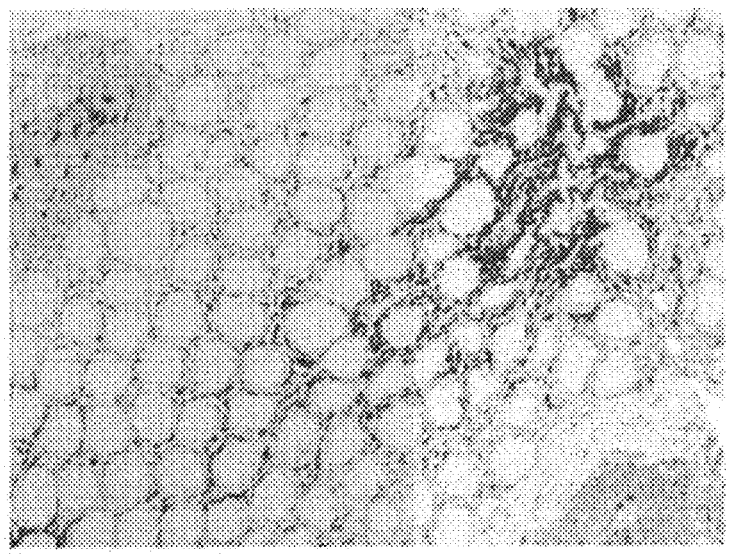
anti-CD68
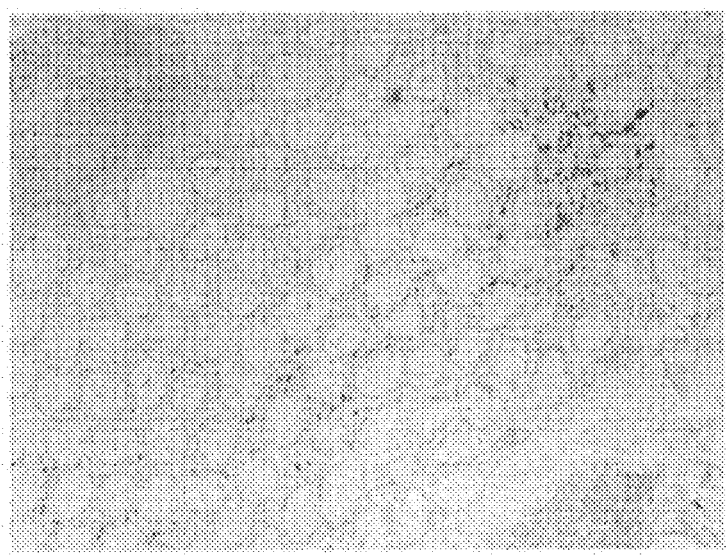
anti-Rep mAb 10-3
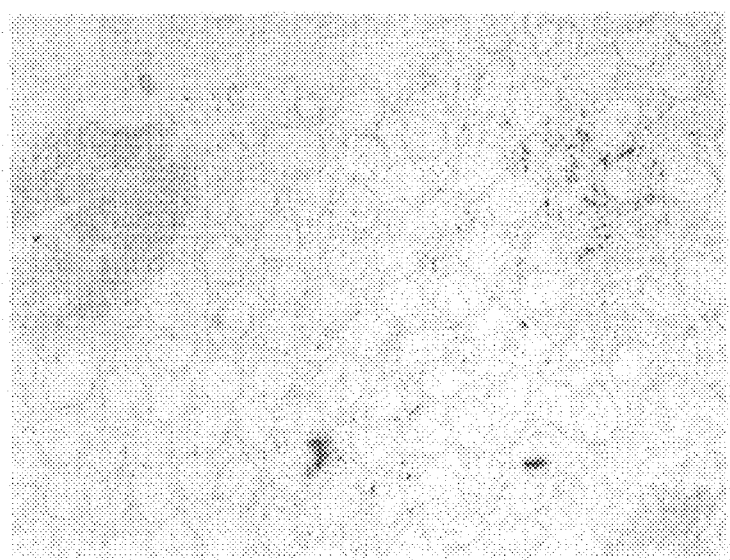
anti-Rep mAb 3-6

USE OF BMMFI Rep PROTEIN AS BIOMARKER FOR COLORECTAL CANCER

RELATED APPLICATIONS AND INCORPORATION BY REFERENCE

This application is a continuation-in-part application of international patent application Serial No. PCT/EP2019/051868 filed 25 Jan. 2019, which published as PCT Publication No. WO 2019/149633 on 8 Aug. 2019, which claims benefit of European patent application Ser. No. 18154190.5 filed 30 Jan. 2018.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been submitted electronically and is hereby incorporated by reference in its entirety. Said ASCII copy is named 00018Sequence_Listing.txt and is 21.2 bytes in size.

FIELD OF THE INVENTION

The invention relates to the use of a DNA-replication-associated (Rep) protein as a biomarker for colorectal cancer.

BACKGROUND OF THE INVENTION

Thousands of people around the world have been diagnosed with colon cancer, many of them ultimately dying of the disease. Patients are typically treated with colon resection surgery, followed by radiation therapy or systemic chemotherapy, the therapy being based on macroscopic traits of the tumor and the tumor stage. The 5-year relapse-free survival rate is improved in some patients receiving chemotherapy after colon surgical resection surgery, while this statistic is not improved in others.

Colorectal cancer (CRC) is the second leading cause of cancer death in the US. Most CRC patients are diagnosed late due to lack of predictive biomarkers and poor screening rate attributable to the inconvenience of current screening methods. To enhance earlier detection, there is a need for biomarkers that will facilitate early detection and further insights into the pathogenesis of CRC.

CRC is a cancer that evolved as a consequence of uncontrolled cell growth in the colon or rectum. These malignancies may develop as a consequence of pre-existing benign adenomas where genetic alterations promote the transition from normal to cancerous growth. Epigenetic events have been recognized as an important mechanism for this transition.

A blood-based protein biomarker panel for the detection of colorectal cancer as described by Fung et al., 2015 has not yet brought the desired results as regards predictability. Thus, unfortunately, there does not exist a biomarker for CRC which may be used both for prognostic and diagnostic purposes.

Citation or identification of any document in this application is not an admission that such document is available as prior art to the present invention.

SUMMARY OF THE INVENTION

In the present application the inventors have created a model for colon cancer development that is shown in FIG. 1.

The inventors found that the uptake of BMMF (Bovine Meat and Milk Factor) agents within the first months of life either by substitution of breast-feeding during weaning by cow milk products or by the uptake of dairy or beef products, in general, leads to the early infection of newborns with BMMF antigens in the colon. Based on the decline of maternal antibodies and the frequently observed weakness of the immune system often coupled with induction of immune tolerances of the newborn during this very early period of life, these agents might either directly escape colonic immune response or a situation of immune tolerance against these agents might be induced. Within the next years or decades—depending on the immune system of the host—more and more BMMF antigens accumulate within the colonic lamina propria. This accumulation may be triggered also by the uptake of specific molecules that may represent receptors for BMWs. These molecules are also taken up by consumption of cow products and are metabolized into receptors on the surface of the host cells. When a certain level of antigen is reached by continuous uptake of BMMFs in combination with focal spreading of infection, the host immune response induces a state of chronic and local inflammation producing a stable increase of reactive oxygen species (ROS) and cyclooxygenase-2 (Cox-2) which dramatically increases the probability of deregulated cell proliferation with concomitant fixation of random mutations in surrounding cells induced by ROS.

Available results based on Ki67 (Ki67=proliferation marker) IHC staining show that especially the basal epithelial cells derived from epithelial stem cells located close to the endpoint of the crypts and migrating towards the distal luminal part of the crypts feature an intrinsically high proliferation enabling stochastic manifestation of mutations as a basic requirement for tumorgenesis and development of colon cancer (FIG. 2). Thus, BMWs represent a specific and local trigger for induction of chronic inflammation within the lamina propria leading to an increase of ROS which induces proliferation and mutation in surrounding epithelial cells eventually leading to the formation of polyps as precursors for colon cancer.

In detail, a selection of 11 pairs of donor tissue samples (each tumor tissue and peripheral tissue) and 4 samples from different donors of colon polyp tissue were subjected to IHC staining with mouse monoclonal anti-Rep antibodies. With regard to the 11 tumor and peripheral samples, 9 out of 11 tissues showed strong specific antibody staining with at least two anti-Rep antibodies. Exemplarily, the staining with an anti-Rep antibody (e.g. antibody 10-3) shows specific detection of protein targets in tissue samples 4798, 4799, 4802, 4806, 4809 and 4813 in the tumor as well as in the peripheral tissue. In general, the staining intensity is higher for peripheral tissue, where intensely stained cytoplasmic aggregates of smaller size concentrate within distinct islands of cells within the lamina propria between the characteristic Crypts of Lieberkuhn of the colon tissue (all pictures showing traversal cuts throughout the Crypts of Lieberkuhn with the (inner) lumen of the crypts having contact to the colonic fluids in the center of the ring-like arrangement of epithelial cells of the crypts; FIG. 2). Staining of tumor tissues also shows intense staining of smaller sized aggregates mainly within the cytoplasmic regions of the stroma cells within the tumor tissue. The same aggregate-like structures are also visible in the lamina propria of colon polyps by the use of four different anti-Rep antibodies for staining of sequential cuts. Both, for colon peripheral tissue and for colon polyps, the regions with highest Rep-specific antibody detection correlate with regions with highest detection levels for CD68 positive cells pointing towards a localization of the Rep-specific antigens in inflammatory islands, i.e. regions with especially high levels of inflammatory monocytes, circulating macrophages, or tissue macrophages.

As additionally shown in the present application, the comparison of Rep IRS scores (IRS, immunoreactive score) of peritumoral and tumoral tissues confirm a significantly increased Rep detection in the peritumoral tissue of the analyzed CRC patients.

The inventors concluded that for cancer induction the amount of BMMF antigen within the lamina propria between the colon crypts is important for the induction of chronic local inflammation, induction of diffusing ROS/NOS which finally induces random mutations in dividing stem and daughter cells of neighboring crypts which might turn into early polyps/tumor precursor cells by manifestation of key mutations. Thus, a correlation of peritumoral BMMF levels and intensity of CD68-positive macrophages should be observable. Indeed, by testing IRS values for Rep-detection against IRS-values for CD68-detection within the corresponding CRC patients, a significant correlation of Rep and CD68 detection is observed which shows that higher detection levels of Rep correlate with higher levels of CD68 detection.

To test a prognostic score of Rep detection in peritumoral regions of CRC patients on patient survival time, Kaplan Meier curves were calculated based on patient data which were grouped into "Rep low" and "Rep high". High levels of Rep in CRC patients correlate with a significant reduction of patient overall survival time, c.f. FIG. 13 and FIG. 14. The experiments show that increased Rep levels correlate with a hazard ratio of 4.7 indicating a negative correlation of Rep detection and patient survival and underlining the prognostic score of Rep detection in CRC tissue. Patients scored "Rep low" show a 5- and 10-year survival probability of 92%, whereas patients with "Rep high" show significantly decreased survival probabilities of 74% after 5 years and 65% after 10 years, representing a decrease of 20 to 30%.

The inventors also tested the antibody level of colon cancer patients by contacting the Rep protein with a serum specimen suspected of containing anti-Rep protein antibodies under conditions that permit the Rep protein to bind to any such antibody present in the specimen. The inventors recognized that the serum reactivity is reduced in colon cancer patients in comparison to healthy controls.

So far a spectrum of 18 different, but partially related, DNA molecules were isolated from different test material (bovine sera, milk, brain tissue of one multiple sclerosis patient autopsies) (Funk, Gunst et al. 2014, Gunst, zur Hausen et al. 2014, Lamberto, Gunst et al. 2014, Whitley, Gunst et al. 2014; WO 2015/062726 A2; WO 2016/005054 A2). The 18 isolates were divided into four different groups BMMF1 through BMMF4, according to their molecular characteristics (zur Hausen et al., 2017). Three of these groups revealed a remarkable degree of similarity to *Acinetobacter baumannii* and Psychrobacter plasmids. The fourth group comprised 3 isolates being representatives of *Gemycirularviridae*. Putative Rep genes were identified as part of the BMMF's DNA sequences obtained by in silico comparisons to available sequences. Amplification using abutting primers in the rep gene led to the isolation of full and partial circular DNA genomes from bovine sera (Funk et al., 2014). This was extended to samples from commercially available milk products for the presence of specific circular single-stranded DNA genomes. Full-length circular single-stranded DNA molecules of 14 different isolates of (~1100 to 3000 nucleotides) were cloned and sequenced (Whitley et al., 2014; Gunst et al., 2014; Funk et al., 2014; Lamberto et al., 2014). Four additional isolates were obtained from human brain and serum (all from patients with multiple sclerosis) (Whitley et al., 2014; Gunst et al., 2014; Lamberto et al., 2014).

Among these isolates two DNA molecules closely related to transmissible spongiform encephalopathy (TSE)-associated isolate Sphinx 1.76 (1,758 bp; accession no. HQ444404, (Manuelidis L. 2011)) were isolated from brain tissue from an MS patient. These isolates were MSBI1.176 (MSBI, multiple sclerosis brain isolate) (1,766 bp) and MSBI2.176 (1,766 bp) which are designated as "MSBI1 genome" and "MSBI2 genome", respectively. MSBI1.176 shares 98% nucleotide similarity to the sequence of Sphinx 1.76. The large open reading frames (ORFs) of the isolates encode a putative DNA replication protein sharing high similarity between them. Another common feature is the presence of iteron-like tandem repeats. The alignment of this repeat region indicates a variation in the core of single nucleotides. This iteron-like repeats may constitute the binding sites for Rep proteins. The sequences of the isolates have been deposited in the EMBL Databank under accession numbers LK931491 (MSBI1.176) and LK931492 (MSBI2.176) (Whitley C. et al. 2014) and have been aligned and described in WO 2016/005054 A2.

Further isolates were obtained from cow milk. These Cow milk isolates (CMI) were CMI1.252, CMI2.214 and CMI3.168 which are designated as "CMI1 genome", "CMI2 genome" and "CMI3 genome", respectively. The sequences of the isolates have been deposited in the EMBL Databank under accession numbers LK931487 (CMI1.252), LK931488 (CMI2.214) and LK931489 (CMI3.168) and have been aligned and described in WO 2016/005054 A2.

The present inventors have found that both CMI genomes and MSBI genomes show a significant production of transcribed RNA and the encoded Rep protein is expressed in peripheral tissue around the colon cancer islands and polyps. The present inventors have found that the encoded Rep proteins (MSBI1 Rep, MSBI2 Rep, CMI1 Rep, CMI2 Rep, CMI3 Rep) represent a biomarker for colon cancer. As DNA-replication-associated protein (RepB) the Rep protein has DNA binding activity and can be essential for initiation of replication of episomal or viral DNA molecules. Rep proteins show a marked potential of self-oligomerization and aggregation, which was described within prokaryotic systems in vivo and in vitro (Giraldo, Moreno-Diaz de la Espina et al. 2011, Torreira, Moreno-Del Alamo et al. 2015).

The inventors have raised monoclonal antibodies against Rep protein. In particular embodiments the anti-Rep antibodies bind to epitopes of Rep protein that are exemplified in FIG. 3. Particular preferred antibodies bind to epitopes within an amino acid sequence selected from the group consisting of amino acids from 1 to 136, from 137 to 229 and from 230 to 324 of SEQ ID NO: 1. For example, the antibody binds to an epitope comprised by SEQ ID NO: 2 or SEQ ID NO: 3.

The invention provides the teaching that Rep proteins may represent biomarkers for an enhanced risk to develop colon cancer and are useful as a marker for determining the overall survival prognosis of CRC patients.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

The Deposits with Leibniz Institute DSMZ-German Collection of Microorganisms and Cell Cultures, Inhoffenstraße 7B, D-38124 Braunschweig, Germany on Sep. 28, 2017 under deposit accession numbers DSM ACC3327, DSM ACC3328, and DSM ACC3329 were made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 4 shows IHC data obtained by employment of antibody 10-3 (Group C anti-Rep antibody) to colon cancer tissue and surrounding non-cancerous peripheral tissue; designations of patients: #4799, #4809, #4798, #4802, #4813 and #4806.

FIG. 5 shows IHC data obtained by employment of anti-Rep antibodies 3-6 and 10-3 (Group C anti-Rep antibodies) and commercially available anti-CD68 antibodies to peripheral tissue surrounding the colon tumour of patient #4809.

DETAILED DESCRIPTION OF THE INVENTION

Figure 1:
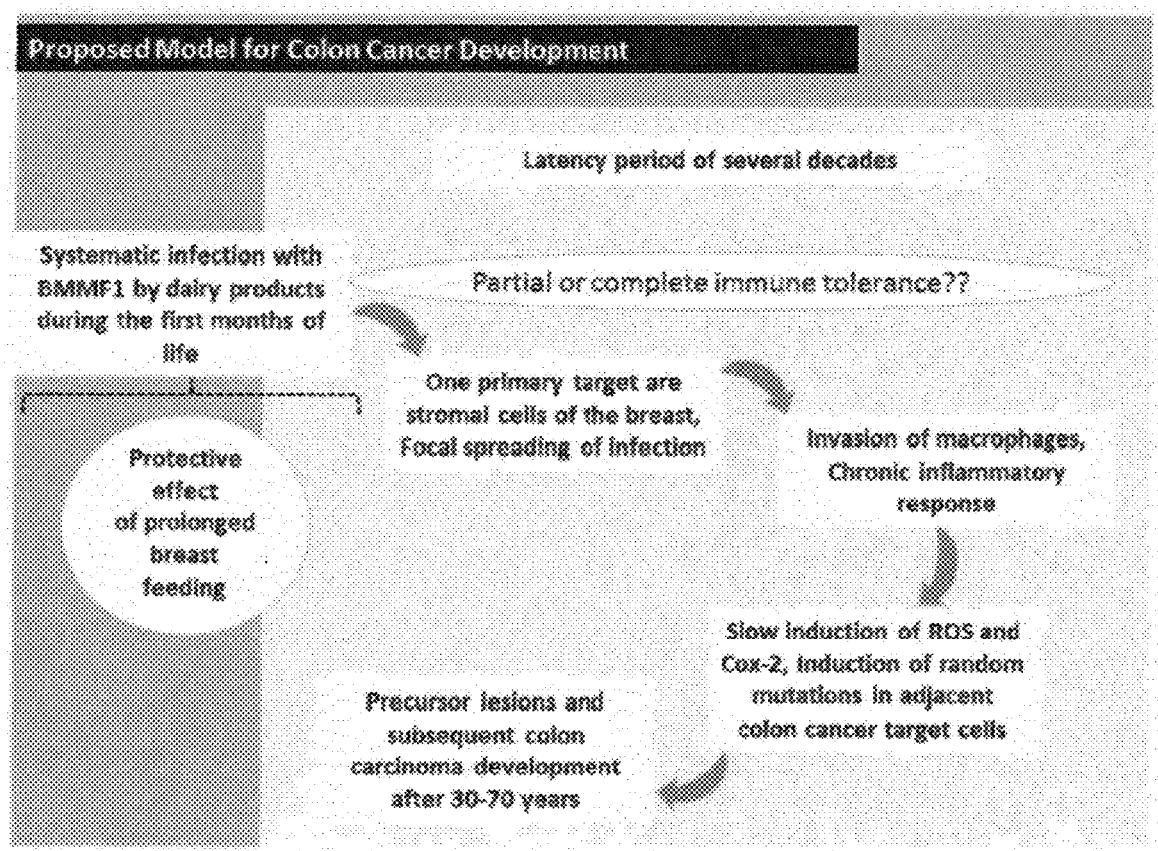
FIG. 1 shows the proposed model for colon cancer development.
Figure 2:
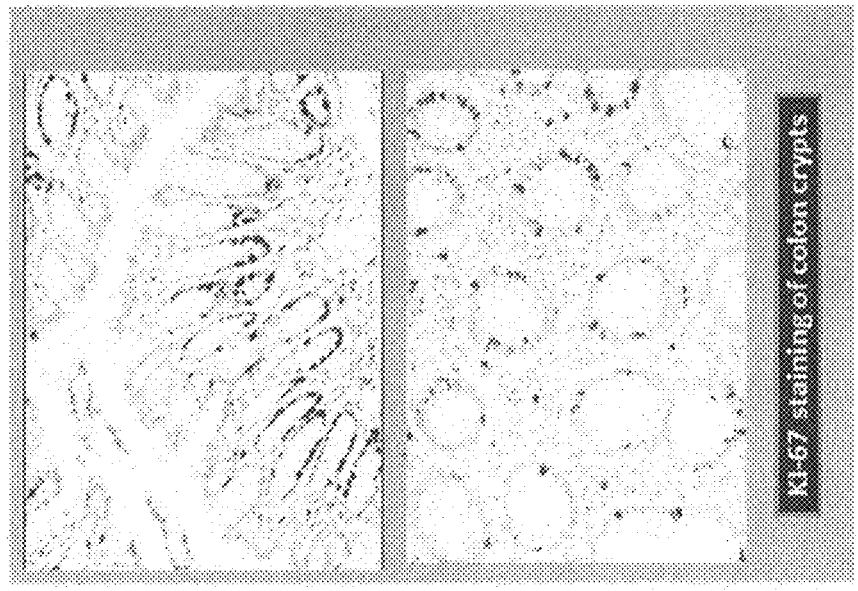
FIG. 2 shows results based on Ki67 IHC staining (available online data). It may be seen that especially the basal epithelial cells derived from epithelial stem cells located close to the endpoint of the crypts and migrating towards the distal luminal part of the crypts feature an intrinsically high proliferation enabling stochastic manifestation of mutations as a basic requirement for tumorgenesis and development of colon cancer.
Figure 3:
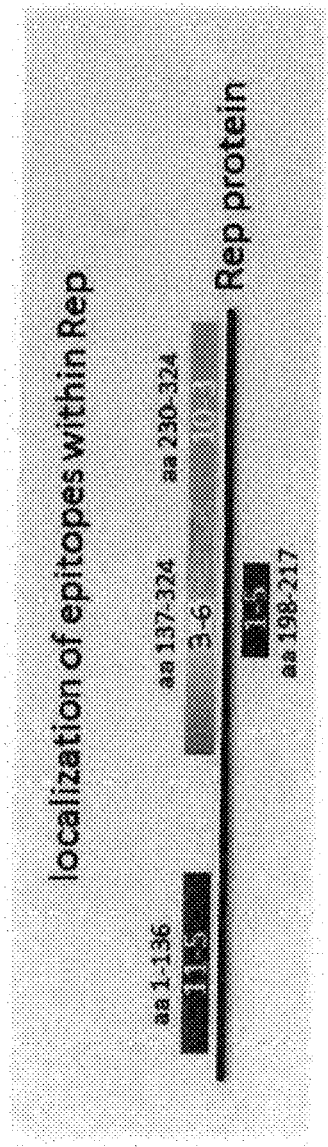
FIG. 3 shows characteristics of the raised antibodies and the localization of epitopes within Rep.
Figure 6:
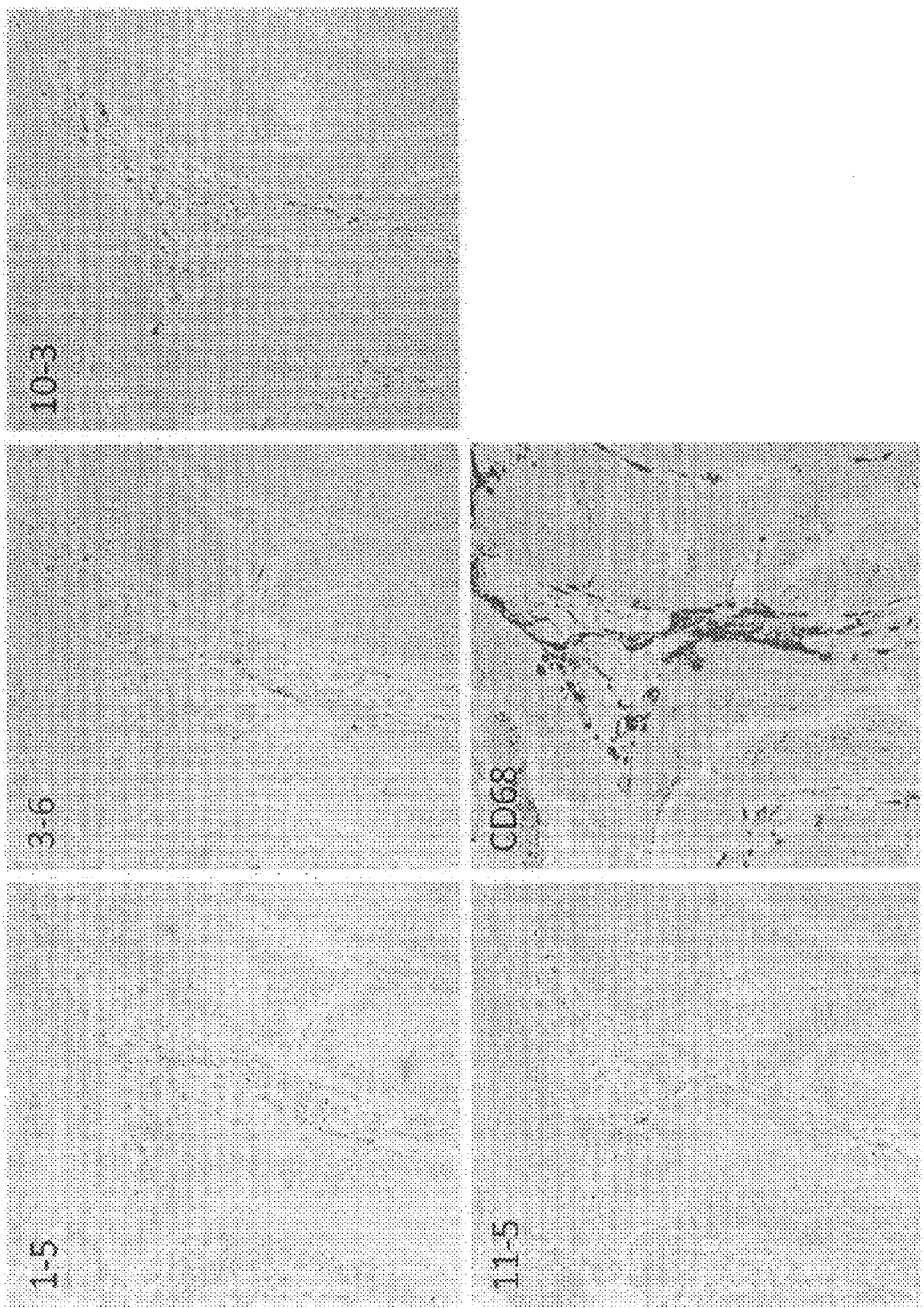
FIG. 6 shows IHC data obtained by employment of anti-Rep antibodies Group A and C antibodies (antibodies 1-5, 3-6, 10-3 and 11-5) and commercially available anti-CD68 antibodies to peripheral tissue surrounding colon benign polyps.

The invention provides the teaching that Rep proteins may represent biomarkers for an enhanced risk to develop colon cancer and are useful as a marker for determining the overall survival prognosis of CRC patients.

The terms "colon cancer" and "colorectal cancer" (CRC) are used interchangeably. CRC is a cancer that evolved as a consequence of uncontrolled cell growth in the colon or rectum. These malignancies may develop as a consequence of pre-existing benign adenomas where genetic alterations promote the transition from normal to cancerous growth. The terms "colon cancer" or CRC mean pre-stages, early stages or late stages of the disease and metastases derived therefrom.

In an alternative embodiment the present invention may also encompass the systematic testing of healthy colonic tissue (tissue from individuals without cancer diagnosis or a specific hint for the disease) to assess the disease risk in the future. This means that the present invention is also suitable to determine the predisposition for developing CRC.

"Rep protein" as used herein refers to a DNA-replication-associated protein (RepB). The Rep protein comprises DNA binding activity and could be essential for initiation of replication of episomal/viral DNA molecules. In general Rep protein refers to a Rep protein from the group of the Small Sphinx Genome (Whitley et al., 2014). In particular, the Rep protein is a MSBI1 genome-encoded Rep protein (MSBI1 Rep), a MSBI2 genome-encoded Rep protein (MSBI2 Rep), a CMI1 genome-encoded Rep protein (CMI1 Rep), a CMI2 genome-encoded Rep protein (CMI2 Rep) or CMI3 genome-encoded Rep protein (CMI3 Rep). Preferably, the MSBI1 Rep protein is encoded by MSBI1.176 deposited in the EMBL databank under the acc. no. LK931491 and has the amino acid sequence as depicted in SEQ ID NO: 1 or the Rep protein is MSBI2 encoded by MSBI2.176 deposited in the EMBL databank under the acc. no. LK931492 and has the amino acid sequence as depicted in SEQ ID NO: 8 (Whitley, Gunst et al. 2014). In another preferred embodiment the CMI1 Rep protein is encoded by CMI1.252 deposited in the EMBL databank under the acc. no. LK931487 and has the amino acid sequence as depicted in SEQ ID NO: 10. In another preferred embodiment the CMI2 Rep protein is encoded by CMI2.214 deposited in the EMBL databank under the acc. no. LK931488 and has the amino acid sequence as depicted in SEQ ID NO: 11. In another preferred embodiment the CMI3 Rep protein is encoded by CMI3.168 deposited in the EMBL databank under the acc. no. LK931489 and has the amino acid sequence as depicted in SEQ ID NO: 12. In a particular preferred embodiment the Rep protein comprises a N-terminal region conserved among BMMF1 genomes consisting essentially of amino acids from 1 to 229 of SEQ ID NO: 1 and a C-terminal variable region specific for MSBI1.176 consisting essentially from amino acids 230 to 324 of SEQ ID NO: 1. The N-terminal conserved region comprises a putative, first DNA binding domain consisting essentially of amino acids from 1 to 136 of SEQ ID NO: 1 and a second putative DNA binding domain consisting essentially of amino acids from 137 to 229 of SEQ ID NO: 1. The C-terminal domain shows little sequence homology with any known protein and consists of amino acids 230 to 324.

"Rep protein" also encompasses fragments and variants of the protein with SEQ ID NO: 1 or SEQ ID NO: 8 which are capable of binding an anti-Rep antibody specific for Rep protein having the amino acid sequence of SEQ ID NO: 1 or SEQ ID NO: 8. Preferably, such a fragment is an immunogenic fragment of the protein having the amino acid sequence of SEQ ID NO: 1 or SEQ ID NO: 8 which encompasses at least one epitope for an anti-Rep protein antibody against the Rep protein of SEQ ID NO: 1 or SEQ ID NO: 8 and, preferably, comprises at least 7, 8, 9, 10, 15, 20, 25 or 50 contiguous amino acids. In particular embodiments the fragment comprises or consists essentially of a domain of the Rep protein, for example, the N-terminal conserved region, the C-terminal variable region, the first or second DNA binding domain. A variant of the protein with SEQ ID NO: 1 or SEQ ID NO: 8 comprises one or more amino acid deletions, substitutions or additions compared to SEQ ID NO: 1 and has a homology of at least 90%, 91%, 92%, 93%, 94%, 95%, 96%, 97%, 98% or 99% to the amino acid sequence of SEQ ID NO: 1 or SEQ ID NO: 8, wherein the variant is capable of binding an anti-Rep antibody specific for a Rep protein having the amino acid sequence of SEQ ID NO: 1 or SEQ ID NO: 8. Included within the definition of variant are, for example, polypeptides containing one or more analogues of an amino acid (including, for example, unnatural amino acids, peptide nucleic acid (PNA), etc.), polypeptides with substituted linkages, as well as other modifications known in the art, both naturally occurring and non-naturally occurring. The term Rep protein includes fusion proteins with a heterologous amino acid sequence, with a leader sequence or with a Tag-sequence and the like. In certain embodiments of the invention protein tags are genetically grafted onto the Rep protein described above, for example the Rep protein selected from the group consisting of MSBI1, MSBI2, CMI1, CMI2 or CMI3. In particular at least one protein tag is attached to a polypeptide consisting of an amino acid sequence as depicted in any one of SEQ ID NOS: 1-3,8-12,14. Such protein tags may be removable by chemical agents or by enzymatic means. Examples of protein tags are affinity or chromatography tags for purification. For example the Rep protein may be fused to a Tag-sequence, for example, selected from the group consisting of $His_6$-Tag (SEQ ID NO: 4), T7-Tag (SEQ ID NO: 5), FLAG-Tag (SEQ ID NO: 6)and Strep-II-Tag (SEQ ID NO: 7). a His-Tag (SEQ ID NO: 4), a T7-Tag (SEQ ID NO: 5), FLAG-Tag (SEQ ID NO: 6) or StrepII-Tag (SEQ ID NO: 7). Further, fluorescence tags such as green fluorescence protein (GFP) or its variants may be attached to a Rep-protein according to the invention.

In a particular preferred embodiment the MSBI1 genome-encoded Rep protein (MSBI1 Rep) is codon-optimized for the production in human cell lines (e.g. HEK-293, HEK293TT, HEK293T, HEK293FT, HaCaT, HeLa, SiHa, CaSki, HDMEC, L1236, L428, BJAB, MCF7, Colo678, any primary cell lines) as well as bovine (e.g. MAC-T) or murine cell lines (e.g. GT1-7). This is described in detail in PCT/EP2017/075774.

The Rep protein of the invention, including the Rep fragments and Rep variants as defined above, can be prepared by classical chemical synthesis. The synthesis can be carried out in homogeneous solution or in solid phase. The polypeptides according to this invention can also be prepared by means of recombinant DNA techniques.

"Subject" as used herein refers to a mammalian individual or patient, including murines, cattle, for example bovines, simians and humans. Preferably, the subject is a human patient.

"Anti-Rep antibody" as used herein refers to an antibody binding at a detectable level to Rep protein which affinity is more strongly to the Rep protein of the invention than to a non-Rep protein. Preferably, the antigen affinity for Rep protein is at least 2 fold larger than background binding. In particular the anti-Rep antibody is specific for the MSBI1 Rep having the amino acid sequence of SEQ ID NO: 1 or MSBI2 Rep. In particular embodiments the antibody is cross-specific for MSBI1 Rep, MSBI2 Rep, CMI1 Rep, CMI2 Rep and/or CMI3 Rep. In certain embodiments the anti-Rep antibody is cross-specific for at least two, preferably all, off MSBI1 Rep, MSBI2 Rep, CMI1 Rep, CMI2 Rep and/or CMI3 Rep.

The inventors also tested the antibody level of colon cancer patients by contacting the Rep protein with a specimen suspected of containing anti-Rep protein antibodies under conditions that permit the Rep protein to bind to any such antibody present in the specimen. Such conditions will typically be physiologic temperature, pH and ionic strength using an excess of Rep protein. The incubation of the Rep protein with the specimen is followed by detection of immune complexes comprised of the antigen. In certain embodiments either the Rep protein is coupled to a signal generating compound, e.g. detectable label, or an additional binding agent, e.g. secondary anti-human antibody, coupled to a signal generating compound is used for detecting the immune complex.

Anti-Rep antibodies can be detected and quantified in assays based on Rep protein as protein antigen, which serves as target for the mammalian, e.g. human, antibodies suspected in the specimen. Preferably, the Rep protein is purified and the specimen can be, for example, serum or plasma. The methods include immobilization of Rep protein on a matrix followed by incubation of the immobilized Rep protein with the specimen. Finally, the Rep-bound antibodies of the formed immunological complex between Rep protein and antibodies of the specimen are quantified by a detection binding agent coupled to a signal generating compound, e.g. secondary HRP-(horseradish-peroxidase)-coupled detection antibody allowing for HRP-substrate based quantification. This signal generating compound or label is in itself detectable or may be reacted with an additional compound to generate a detectable product.

Design of the immunoassay is subject to a great deal of variation, and many formats are known in the art. Protocols may, for example, use solid supports, or immunoprecipitation. Most assays involve the use of binding agents coupled to signal generating compounds, for example labelled antibody or labelled Rep protein; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be in a heterogeneous or in a homogeneous format, and of a standard or competitive type. Both standard and competitive formats are known in the art.

In an immunoprecipitation or agglutination assay format the reaction between the Rep protein and the anti-Rep antibody forms a network that precipitates from the solution or suspension and forms a visible layer or film of precipitate. If no anti-Rep antibody is present in the specimen, no visible precipitate is formed.

In further embodiments the inventors used methods wherein an increased amount of Rep protein in a sample correlates with a diagnosis or predisposition of colon cancer. In such embodiments the Rep protein in the sample is detected by anti-Rep antibodies.

"Sample" as used herein refers to a biological sample encompassing cancerous colon tissue, peripheral tissue surrounding the cancerous colon tissue and (benign) colon polyps. The samples encompass tissue samples such as tissue cultures or biopsy specimen.

Such methods comprise the steps of detecting Rep protein in a sample from a subject by anti-Rep antibodies. In such methods Rep protein is detected in tissue samples by immunohistochemical methods or immunofluoresence microscopy.

In certain embodiments anti-Rep antibodies are used for the detection or capturing of the Rep protein in the sample.

The term "antibody", preferably, relates to antibodies which consist essentially of pooled polyclonal antibodies with different epitopic specificities, as well as distinct monoclonal antibody preparations. As used herein, the term antibody (Ab) or monoclonal antibody (Mab) is meant to include intact immunoglobulin molecules as well as antibody fragments (such as, for example, Fab and F(ab')2 fragments) which are capable of specifically binding to Rep protein. Fab and F(ab')2 fragments lack the Fc fragment of intact antibody, clear more rapidly from the circulation, and may have less non-specific tissue binding than an intact antibody. Thus, these fragments are preferred, as well as the products of a FAB or other immunoglobulin expression library. Moreover, antibodies useful for the purposes of the present invention include chimeric, single chain, multifunctional (e.g. bispecific) and humanized antibodies or human antibodies.

In certain embodiments the antibody or antigen binding fragment thereof is coupled to a signal generating compound, e.g., carries a detectable label. The antibody or antigen binding fragment thereof can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

Anti-Rep antibodies are, preferably, raised (generated) against a Rep protein having the amino acid sequence of SEQ ID NO: 1 or SEQ ID NO: 8 or a fragment thereof by methods well known to those skilled in the art.

In certain embodiments anti-Rep antibodies are used in the methods of the invention which are capable of binding to several or all kinds of Rep proteins from the group of the Small Sphinx Genome (anti-Small-Sphinx-like Rep antibody or anti-SSLRep antibody). Such anti-SSLRep antibody binds to an epitope within the conserved N-terminal region of the Rep protein from amino acids 1 to 229 of SEQ ID NO: 1. In particular embodiments anti-Rep antibodies of the anti-SSLRep type are used which bind to an epitope within SEQ ID NO: 2 (amino acids 32-49 of SEQ ID NO: 1) or SEQ ID NO: 3 (amino acids 197-216 of SEQ ID NO: 1). The peptide fragments of SEQ ID NO: 2 and SEQ ID NO: 3 are highly conserved among the Rep proteins from the Small Sphinx Genome group and appear to be exposed due to their hydrophilic character. Anti-Rep antibodies of the anti-SSL-Rep type may be produced by immunization, for example of mice or guinea pig, by peptides consisting essentially of the amino acid sequences as depicted in SEQ ID NOS: 2 or 3; or by other immunogenic fragments, preferably comprising at least 8-15 amino acids, derived from the conserved N-terminal Rep protein region from amino acids 1 to 229 of SEQ ID NO: 1.

In further embodiments anti-Rep antibodies specific for MSBI1 Rep protein are used. Such antibodies may be produced, for example, by immunization of a mammal such as mice or guinea pig with a full-length Rep protein having the amino acid sequence of SEQ ID NO: 1.

Preferably, the methods of the invention use anti-Rep antibodies which are capable of detecting Rep protein up to ranges from picogramm to femtogramm.

Examples of such groups of anti-Rep antibodies are shown in Table 1:

| Antibody Group | Rep-Protein Localisation | Specificity | Antibody | DSMZ deposit |
|---|---|---|---|---|
| Group A | cytoplasm + nuclear membrane (+nucleus) | MSBI1 + small-sphinx-like All BMMF1 Reps | AB01 523-1-1 (Ab 1-5) | DSM ACC3327 |
| Group B | speckles in cytoplasm | MSBI1 + small-sphinx-like | AB02 304-4-1 (Ab 5-2) | DSM ACC3328 |
| Group C | cytoplasm + nuclear membrane (+nucleus) | MSBI1 specific | MSBI1 381-6-2 (Ab 3-6) MSBI1 572-13-19 (Ab 10-3) MSBI1 617-1-3 (Ab 11-5) | DSM ACC3329 |
| Group D | speckles in cytoplasm | MSBI1 specific | D1: MSBI1 961-2-2 D2: MSBI1 761-5-1 (Ab 13) | DSM ACC3331 DSM ACC3330 |

Anti-Rep antibodies of group A have an epitope within the amino acid sequence depicted in SEQ ID NO: 3 (aa 198-217 of SEQ ID NO: 1) and are capable of detecting MSBI1 Rep and Rep proteins comprising this conserved epitope of the Small Sphinx Genome group (e.g. MSBI2, CMI1, CMI4). In immunofluoresence assays such anti-Rep antibodies detect a specific Rep localisation pattern, wherein the main localisation is homogeneously distributed over the cytoplasm and nuclear membrane; and additional weak and homogeneously distributed localisation is seen in the nucleus. An example of such a group A antibody is antibody AB01 523-1-1 (also called antibody 1-5; DSM ACC3327) which was employed in the examples as group A antibody.

Anti-Rep antibodies of group B have an epitope within the amino acid sequence depicted in SEQ ID NO: 2 (aa 33-50 of SEQ ID NO: 1) and are capable of detecting MSBI1 Rep and Rep proteins comprising this conserved epitope of the Small Sphinx Genome group (e.g. MSBI2, CMI1, CMI4). In immunofluoresence assays such anti-Rep antibodies detect specifically speckles (cytoplasmatic aggregations) of the Rep protein (often in the periphery of the nuclear membrane). An example of such a group B antibody is the antibody designated as AB02 304-4-1 (also called antibody 5-2; DSM ACC3328) which was employed in the examples as group B antibody.

Anti-Rep antibodies of group C detect specifically a structural epitope of MSBI1 (SEQ ID NO: 1). In immunofluoresence assays such anti-Rep antibodies detect a specific Rep localisation pattern, wherein the main localisation is homogeneously distributed over the cytoplasm and nuclear membrane; and additional weak and homogeneously distributed localisation is seen in the nucleus. An example of such a group C antibody is antibody MSBI1 381-6-2 (also called antibody 3-6; DSM ACC3329) which was employed in the Example as group C antibody with an epitope in the sequence of aa 137-324. Another example of an antibody of a group C antibody is antibody MBSI1 572-13-19 (also called antibody 10-3) detecting an epitope in the C-terminal domain of MSBI 1 Rep (aa 230-324). Another example of an antibody of a group C antibody is antibody MBSI1 617-1-3 (also called antibody 11-5) detecting an epitope in the N-terminal domain of MSBI 1 Rep (aa 1-136).

Anti-Rep antibodies of group D detect specifically a structural epitope of MSBI1 (SEQ ID NO: 1), where antibody MSBI1 961-2-2 designated as "D1" (DSM ACC3331) detects an epitope depicted in SEQ ID NO: 9 (aa 281-287) in the C-terminal domain of MSBI1. Antibody MSBI1 761-5-1 (also called antibody 13; DSM ACC3328) designated as "D2" detects a 3D structural epitope of MSBI1 which is exclusively accessible under in vivo conditions and is not accessible in Western Blots. In immunofluoresence assays such anti-Rep antibodies detect specifically speckles (cytoplasmatic aggregations) of the Rep protein (often in the periphery of the nuclear membrane.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Detection of BMMF Protein Targets in Colon Tissue

Anti-Rep antibodies 10-3 (1:500 dilution), 3-6 (1:500), 11-5 (1:100) and 1-5 (1:100) were used for detection of BMW-Rep related protein targets in colon tissue based on immunohistochemistry (IHC). CD68-specific staining of monocytes, circulating macrophages, and tissue macrophages was performed based on an rabbit anti-CD68 antibody (Cell Signaling Technology Europe BV, Catalogue #76437, 1:800). Therefore paraffin embedded tissue sections of colon tissue samples were incubated with the respective antibody on a Leica BOND automated IHC staining system (EDTA epitope retrieval buffer). Colorimetric staining was performed with the Leica DAB staining kit (Leica biosystems, rabbit anti-mouse secondary antibody ab125904 (1:500) from Abcam). The stained tissue sections were digitalized on a Zeiss optical light microscope.

A selection of 11 pairs of donor tissue samples (each tumor tissue and peripheral tissue) and 4 samples from different donors of colon polyp tissue were subjected to IHC staining with mouse monoclonal anti-Rep antibodies. With regard to the 11 tumor and peripheral samples, 9 out of 11 tissues showed strong specific antibody staining with at least two anti-Rep antibodies. Exemplarily, the staining with antibody 10-3 shows specific detection of protein targets in tissue samples 4798, 4799, 4802, 4806, 4809 and 4813 in the tumor as well as in the peripheral tissue. In general, the staining intensity is higher for peripheral tissue, where intensely stained cytoplasmic aggregates of smaller size concentrate within distinct islands of cells within the lamina propria between the characteristic Crypts of Lieberkuhn of the colon tissue (all pictures showing traversal cuts throughout the Crypts of Lieberkuhn with the (inner) lumen of the crypts having contact to the colonic fluids in the center of the ring-like arrangement of epithelial cells of the crypts).

Staining of tumor tissues also shows intense staining of smaller sized aggregates mainly within the cytoplasmatic regions of the stroma cells within the tumor tissue. The same aggregate-like structures are also visible in the lamina propria of colon polyps by the use of four different anti-Rep antibodies for staining of sequential cuts. Both, for colon peripheral tissue and for colon polyps, the regions with highest Rep-specific antibody detection correlate with regions with highest detection levels for CD68 positive cells pointing towards a localization of the Rep-specific antigens in regions with especially high levels of inflammatory monocytes, circulating macrophages, or tissue macrophages.

For verification of IHC results, part of the patient tissue material was lysed in 8M urea denaturing lysis buffer with a tissue homogenizer and subjected to SDS-PAGE. The areas of interest were cut, tryptically digested and analyzed by mass spectroscopy for the presence of BMMF1 specific peptide targets. A set of 4 pairs (tumor and peripheral tissue) with strong IHC signal levels was chosen together with one pair with no IHC signal. In line with the IHC results, only the 4 strongly IHC-positive peripheral tissues allowed for Mass-Spec detection of one BMMF1-group-specific peptide sequence.

To confirm specificity of the antibody detection in IHC, DNA isolations from the five samples with strongest IHC signal detection were subjected to rolling circle amplification and PCR with BMMF-group1 specific primers and DNA sequencing to analyze the presence of BMMF DNA in the same tissue material. Indeed, based on a set of the 5 strongest IHC sample pairs (tumor and peripheral tissue), within each donor MSBI1-specific DNA was isolated from at least one tissue type (tumor or peripheral tissue).

Example 2: Immunohistochemical Staining of CRC Tissue Multi Arrays (TMAs)

The detection of BMMF1 Rep protein antigens in tissue material of patients with colorectal cancer (CRC) was tested based on immunohistochemical staining of CRC tissue multi arrays (TMAs) with a specific mouse monoclonal anti-BMMF1 Rep antibody. Therefore, TMAs representing a total of 259 CRC patients were used, which offered a total of each two tissue spots of tumoral as well as two spots of peritumoral tissue regions per patient. All patients were treated in the University Hospital in Heidelberg in 2003 and 2004. The TMA samples were provided by the tissue bank of the National Center for Tumor Diseases (NCT, Heidelberg, Germany) in accordance with the regulations of the tissue bank and the approval of the ethics committee of Heidelberg University by permission of Hermann Brenner, Michael Hoffmeister and Jenny Chang-Claude (Tissue Bank of the National Center for Tumor Diseases (NCT) Heidelberg, Germany and Institute of Pathology, Heidelberg University Hospital, Germany).

Tissue staining. The TMAs were stained fully automatically on a BOND MAX machine (Leica Biosystems) with EDTA epitope retrieval and the given antibody incubations (Table 2). Detection was performed by using Bond Polymer Refine Detection Kit (D59800 Leica DAB Kit) including DAB chromogen and hematoxylin counterstain. Slides were scanned with a digital slide scanner (Hamamatsu) and analyzed based on Hamamatsu NDP viewer software.

Table 2. Experimental parameters used for IHC staining.

TABLE 2

Experimental parameters used for IHC staining

| Antibody | Source | Host | Dilution | Final concentration in µg/ml | Incubation time |
|---|---|---|---|---|---|
| Primary | | | | | |
| Rep mAb #3-6 | T. Bund, DKFZ | mouse | 1:500 | 3.9 | 30 min at room temperature |
| CD68 | Cell signaling #76437 | rabbit | 1:1000 | | |
| Secondary | | | | | |
| rabbit anti-mouse | Abcam #125904 | rabbit | 1:500 | | 20 min at room temperature |

BMMF Signal quantification. Two researchers independently scored the tissues spots according to the following scoring criteria. For each antibody, the percentage of stained cells (positivity) and intensity (I) were determined. For Rep staining only stromal staining was evaluated representing the dominant localization of detected BMMF antigen with negligible stainings in tumor region in tumoral tissues spots or crypts in peritumoral spots. The positivity (POS) of Rep staining was assessed using a three-level scale in which 0 indicated no positive tissue parts at all, 1 indicated 1-10% positive, 2 indicated 11-30%, 3 indicated more than 30% of the individual tissue spots showing stained aggregates. For CD68/macrophage staining the positivity score was set as 0 for negative tissue spots, 1 indicated<20% positive cells, 2 indicated 20-60%, 3 indicated more than 60% of positive cells. Intensity (I) was generally graded as follows: 0=no reaction, 1=mild, 2=intense staining. For statistical analysis the immunoreactive score IRS was calculated as follows:

$$IRS=[(I(Investigator_1)+I(Investigator_2))/2]*[(POS(Investigator_1)+POS(Investigator_2))/2];$$ minimum value=0, maximum value=6.

An overview is shown in Table 3. Out of 259 patients, 12 patients were excluded because of bad tissue quality and one because of missing clinical data. In total, data from 246 patients was processed for further analysis.

TABLE 3

Parameters used for quantification of TMA staining (IRS: Immunoreactive Score).

| | Intensity (I) | I | Positivity (proportion of positive cells, POS) | POS |
|---|---|---|---|---|
| Rep staining | 0 | no reaction | 0 | 0 |
| | 1 | mild | 1 | 1-10% |
| | 2 | strong | 2 | 11-30% |
| | | | 3 | >31% |
| CD68 staining | 0 | no reaction | 0 | 0 |
| | 1 | mild | 1 | <20% |
| | 2 | strong | 2 | 20-60% |
| | | | 3 | >60% |

IRS = [(I(Investigator1) + I(Investigator2))/2]*[(POS(Investigator1) + POS(Investigator2))/]

Statistical analysis. Statistical analysis was performed using R-3.5.2 r-project.org and R-studio 2016. In order to compare tumoral and peritumoral tissue a 2-sided Wilcoxon signed rank test was performed. Interdependence between immunostaining and clinical data was calculated using Kruskal-Wallis test. Survival curves were plotted using the Kaplan-Meier method and analyzed using the log-rank test. Hazard ratio was determined by Cox-regression analysis. P-Values less than 0.05 were considered to be statistically significant.

Figure 7:
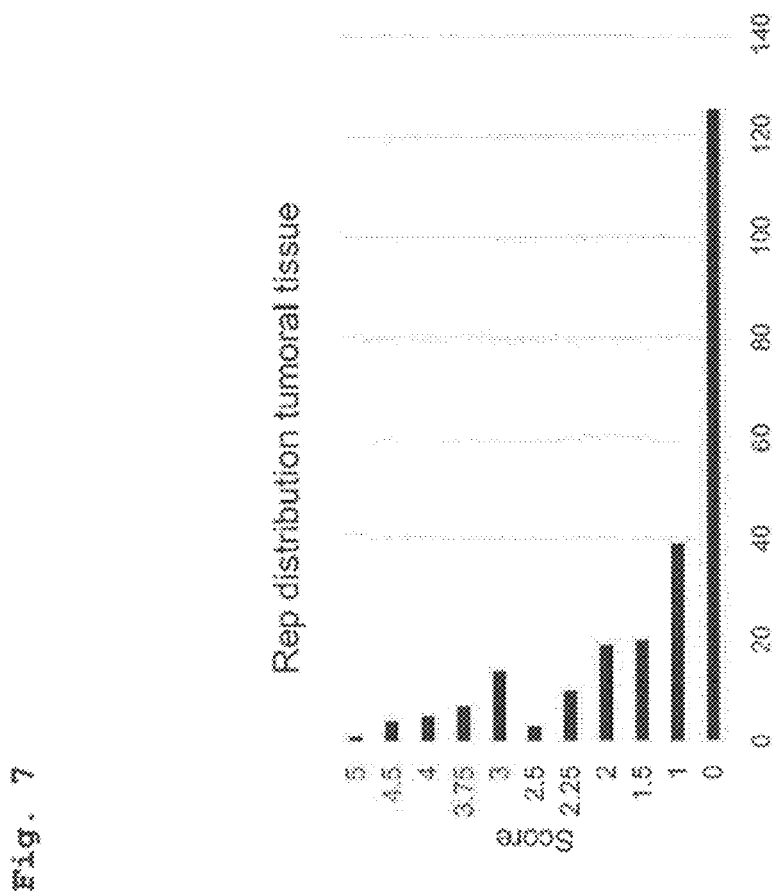
FIG. 7 shows distribution of IRS values for immunohistochemical staining of tumoral tissue region of CRC patients with an anti-Rep antibody.
Figure 8:
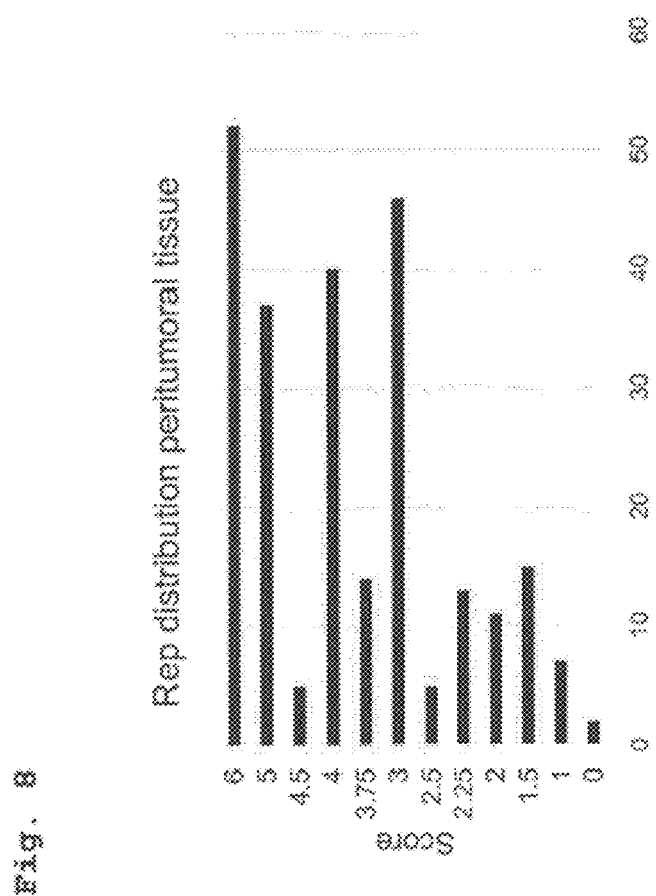
FIG. 8 shows distribution of IRS values for immunohistochemical staining of peritumoral tissue region of CRC patients with an anti-Rep antibody.

Results. In total, scoring information was collected for n=246 CRC patients. In Rep scorings for tumoral tissue regions 49.3% of the patient tissues showed positivity, while scorings for peritumoral tissues showed 99.1% of the patient tissues to be positive. The corresponding distributions of IRS values shows an asymmetric distribution for the tumoral tissue with an enrichment of cases with IRS values of 0 and 1 (FIG. 7). This trend is inverted for the distribution of the IRS values for the peritumoral scoring with an enrichment of IRS values of >3 (FIG. 8).

Figure 9:
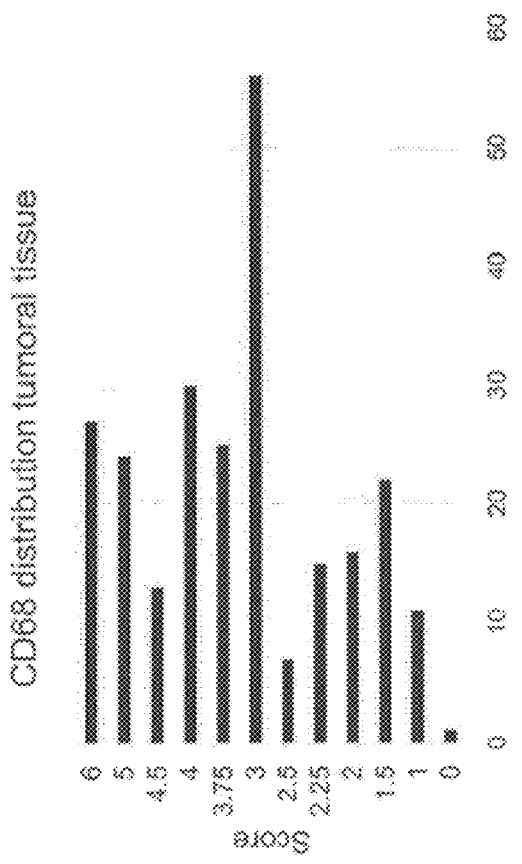
FIG. 9 shows distribution of IRS values for immunohistochemical staining of tumoral tissue region of CRC patients with an anti-CD68 antibody.
Figure 10:
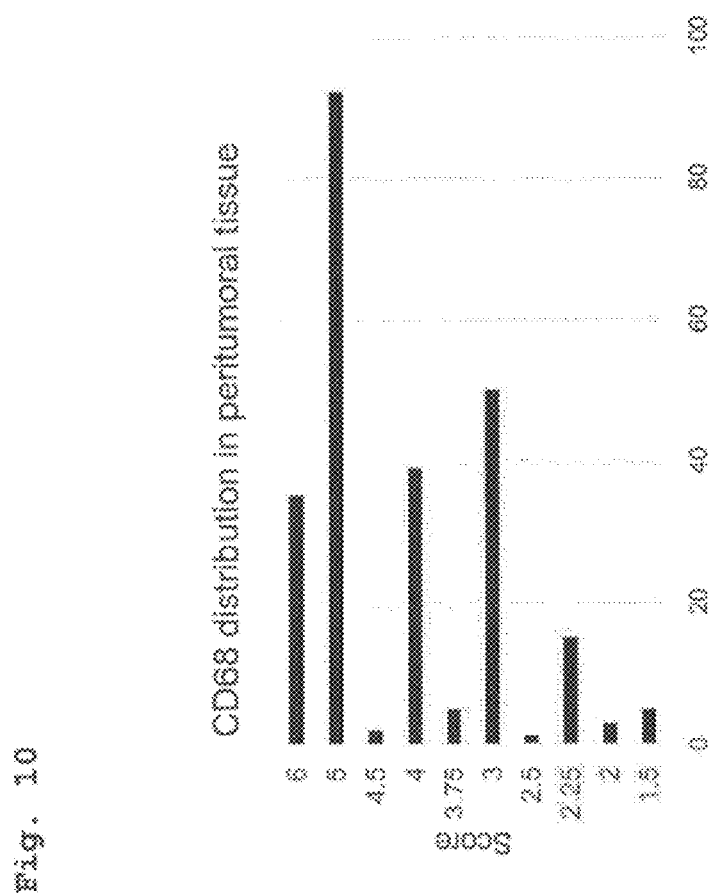
FIG. 10 shows distribution of IRS values for immunohistochemical staining of peritumoral tissue region of CRC patients with an anti-CD68 antibody.

With respect to the quantification of signal obtained by staining of tumoral (FIG. 9) and peritumoral tissue regions (FIG. 10) with CD68 antibodies >99% of the patients showed positivity with a balanced distribution of IRS values in both cases.

Figure 11:
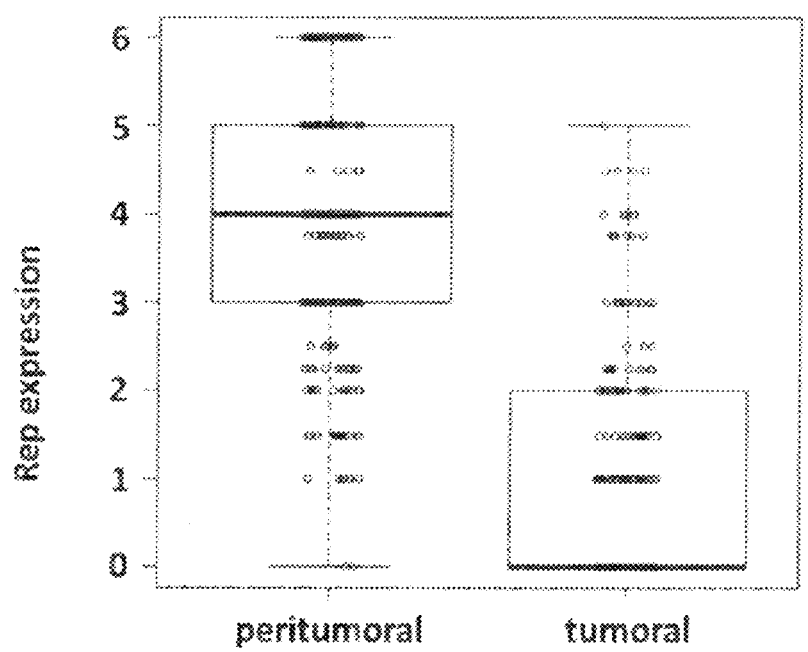
FIG. 11 shows representation of IRS values for peritumoral and tumoral tissues of CRC patients.

Comparison of Rep IRS scores of peritumoral and tumoral tissues suggested a significantly increased Rep detection (p=>2.2e−16) in the peritumoral tissue of the analyzed CRC patients (FIG. 11).

Figure 12:
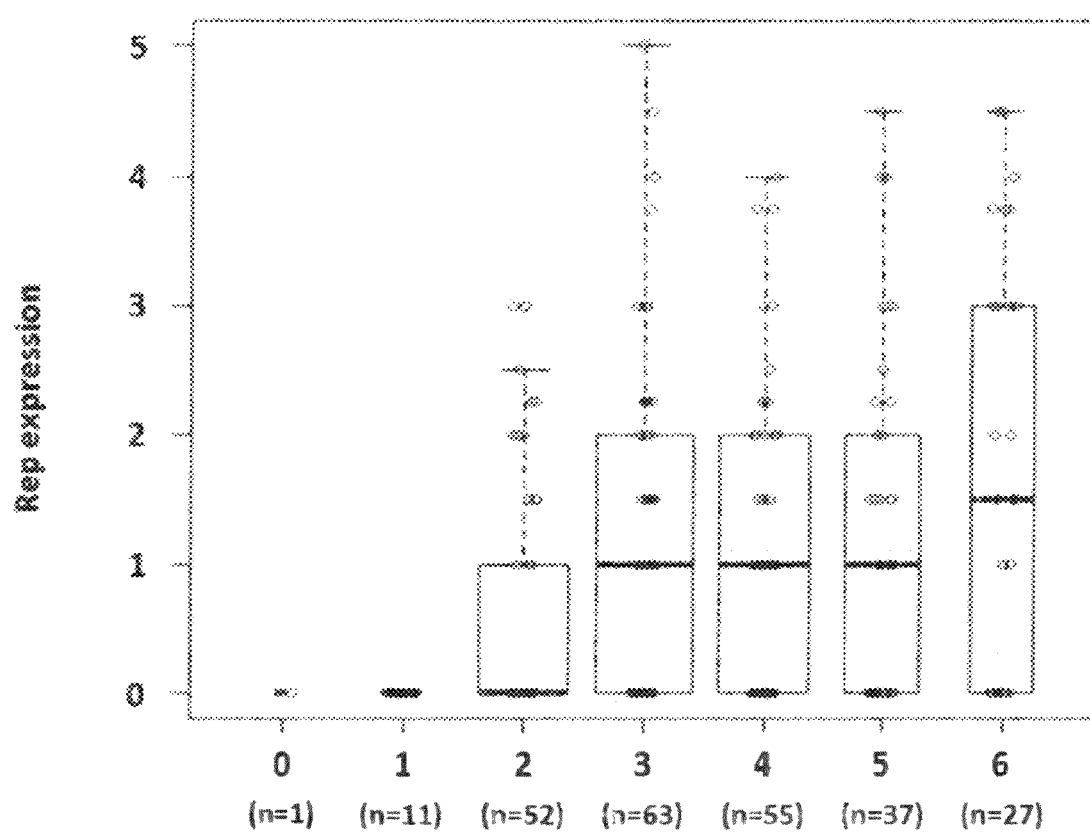
FIG. 12 shows IRS values of Rep detection are plotted against CD68 positivity, which is grouped into 7 levels (0-6).

The inventors concluded that for cancer induction the amount of BMW antigen within the lamina propria between the colon crypts is important for the induction of chronic local inflammation, induction of diffusing ROS/NOS which finally induces random mutations in dividing stem and daughter cells of neighboring crypts which might turn into early polyps/tumor precursor cells by manifestation of key mutations. Thus, a correlation of peritumoral BMMF levels and intensity of CD68-positive macrophages should be observable. Indeed, by testing IRS values for Rep-detection against IRS-values for CD68-detection within the corresponding CRC patients, a significant correlation of Rep and CD68 detection is observed (p=0.00045 by Kruskal Wallis test), which shows that higher detection levels of Rep correlate with higher levels of CD68 detection (FIG. 12).

Figure 13:
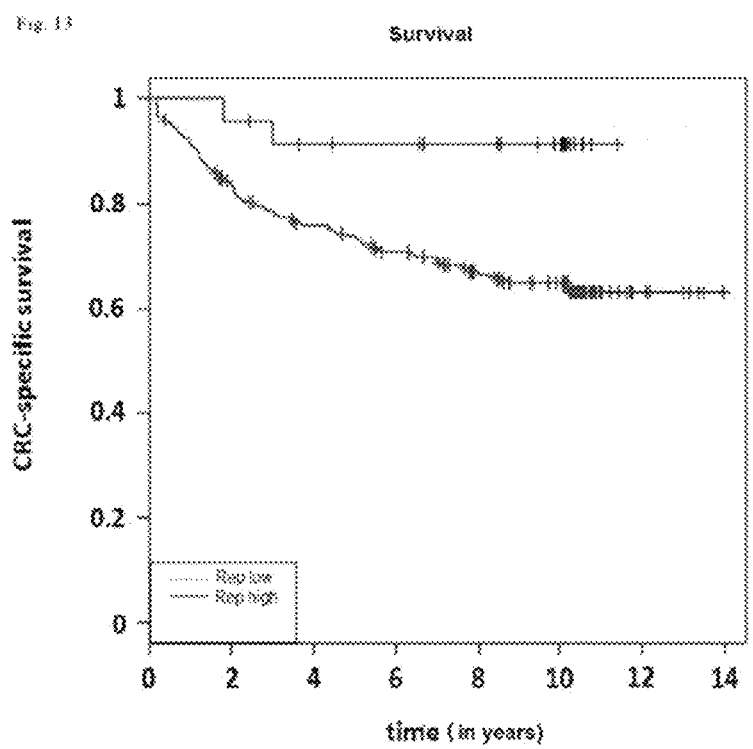
FIG. 13 shows Kaplan-Meier representation of survival of CRC patients grouped into "Rep low" (IRS values 0-1.9) and "Rep high" (IRS values 2-6).

To test a prognostic score of Rep detection in peritumoral regions of CRC patients on patient survival time, Kaplan Meier curves were calculated based on a set of n=243 patients (77 events based on CRC-specific death, 166 censored), which were grouped into "Rep low" for IRS values of 0-1.9 and "Rep high" for IRS values of 2-6 (FIG. 13). High levels of Rep in CRC patients correlate with a significant reduction of patient overall survival time (p=0.0017).

Figure 14:
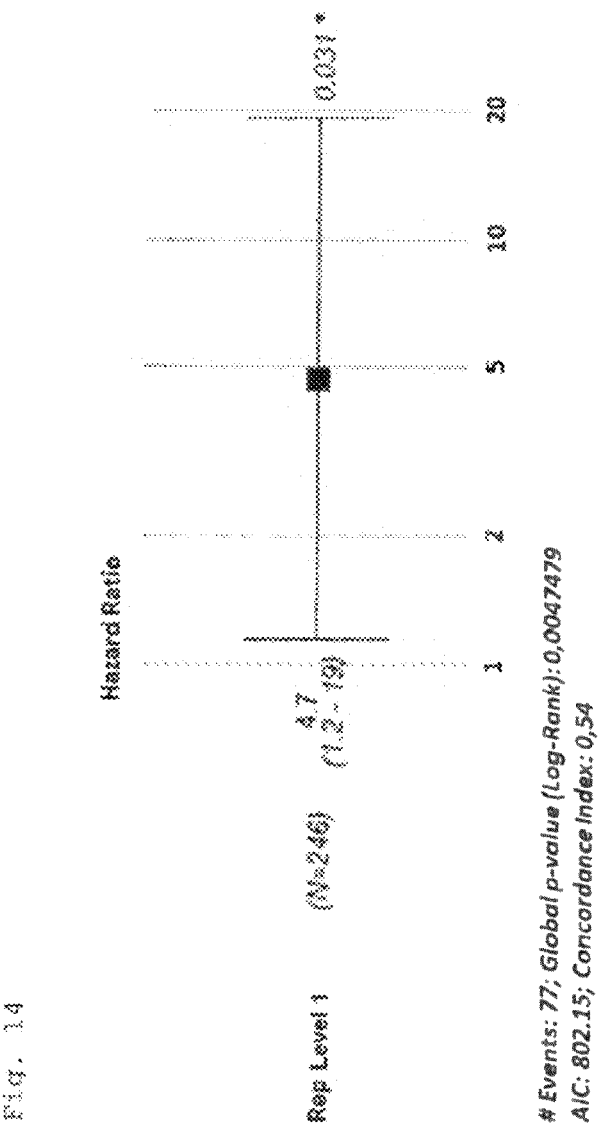
FIG. 14 shows representation of the prognostic Hazard Ratio of Rep detection in peritumoral CRC patient tissues based on Cox-correlation of Kaplan-Meier survival curves of CRC patients grouped into "Rep low" (IRS values 0-1.9) and "Rep high" (IRS values 2-6).

Increased Rep levels correlate with a hazard ratio of 4.7 (95% CI: 1-19) indicating a negative correlation of Rep detection and patient survival (p=0.00475) and underlining the prognostic score of Rep detection in CRC tissue (FIG. 14).

Figure 15:
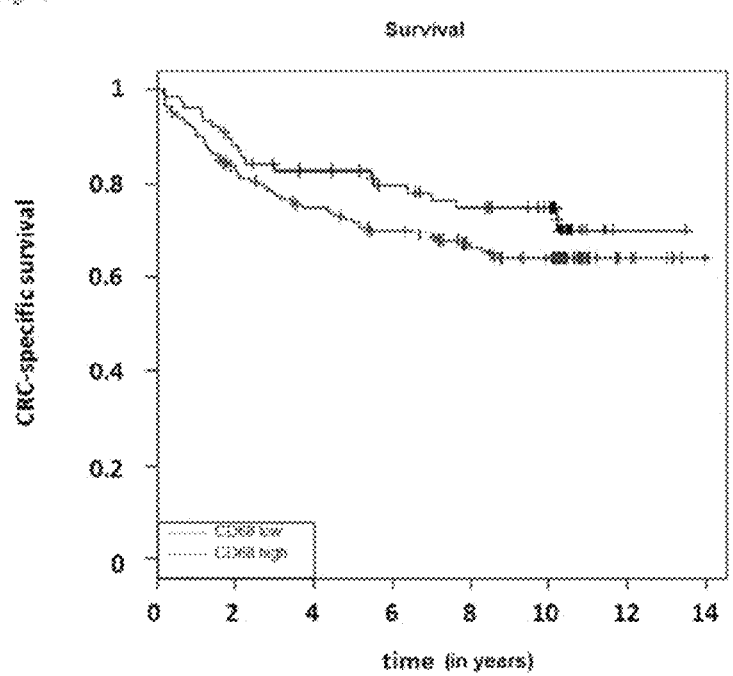
FIG. 15 shows Kaplan-Meier representation of survival of CRC patients grouped into "CD68 low" (IRS values 0-2.9) and "CD68 high" (IRS values 3-6).

Patients scored "Rep low" show a 5 and 10-year survival chance of 92%, whereas patients with "Rep high" show chances of 74% after 5 years and 65% after 10 years, representing a decrease of 20 to 30%. The prognostic effect of Rep detection is not explainable by CD68 detection, as survival analysis based on "CD68 high" and "CD68 low" Kaplan Meier analysis shows no significant differences between the two survival curves (p=0.271, n.s.)(FIG. 15).

Figure 16:
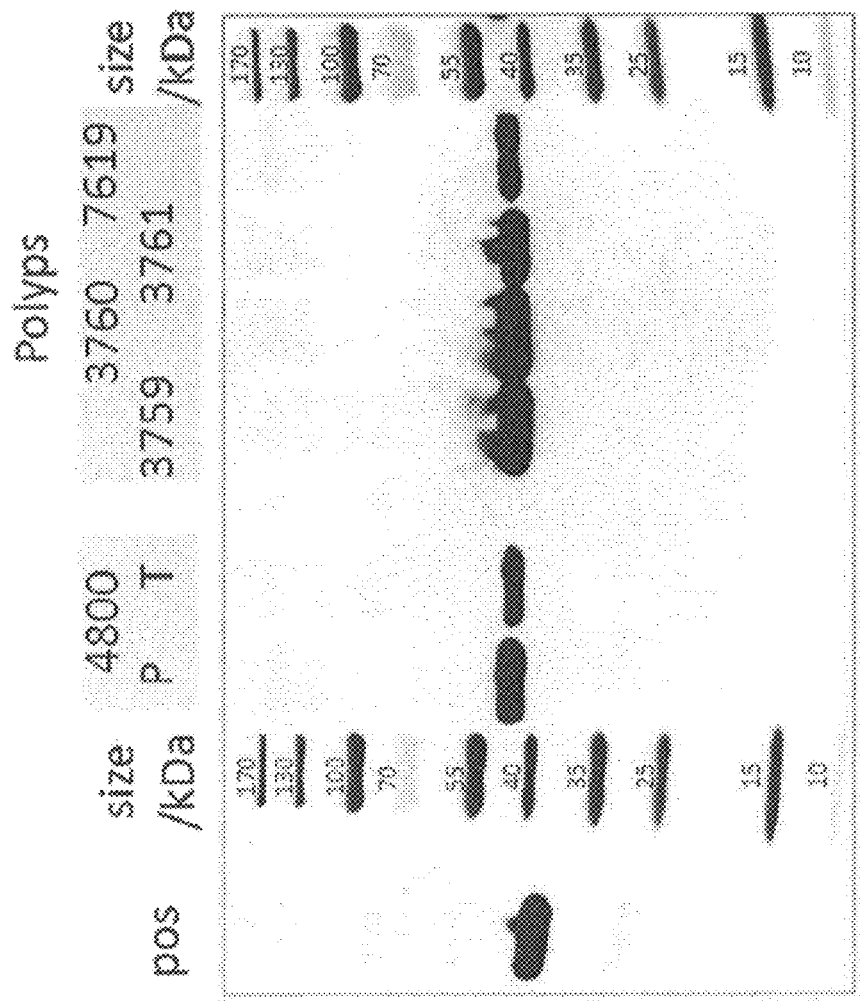
FIG. 16 shows immunodetection of BMMF-Rep antigens in tissue lysate of an exemplary CRC patient (peritumoral and tumoral) as well as of four polyps of individual donors after immunostaining with anti-BMMF-Rep antibody 5-2. 100 ng affinity-purified MSBI1.176 Rep protein was loaded as positive control.

Example 3: Detection of BMMF Rep Antigens by Immunoblotting of Tissue Lysates of CRC Patients Peritumoral or tumoral tissue material of the same patient (e.g. patient 4800 P (peritumoral) or 4800 T (tumoral)) or tissue material form early polyps of four individual donors was lysed in 8 M urea, 100 mM NaH2PO4, 10 mM Tris, 5 mM DTT, pH 8.0 with the use of protease inhibitors (P8340 Sigma-Aldrich) in a tissue homogenizer at 4° C. with silica beads before SDS-PAGE and immunodetection with anti-BMW Rep antibodies, in particular anti-Rep Ab 5-2 (1:250 dilution). Target bands at around 42 kDa were clearly visible with strongest intensities for the peritumoral CRC patient sample 4800 and even stronger bands for tissue lysates of early polyps of the four individual patients (FIG. 16).

Example 4: PCR Amplification of BMMF Rep DNA

In addition, laser microdissection of immunohistochemically stained peritumoral tissue regions of CRC patients (anti-Rep Ab 3-6) and following DNA preparation led to the identification of full-length MSBI1.176 BMMF DNA in all three patients tested (4799, 4808 and 4809). Therefore, total DNA was prepared from the dissected tissue regions by over-night incubation of the dissected tissue with 25 μl of a 5% suspension of Chelex beads (Bio-Rad Cat #142-1253), 5 protease at 750 rpm on a thermomixer. The suspension was vortexed for 10 s at maximum speed, then placed in a thermomixer at 99° C. for 8 min. The suspension was then centrifuged for 5 min at 12.000 g at room temperature to pellet the Chelex resin. 1 μl of the supernatant was used for rolling circle amplification (RCA) with phi29 DNA Polymerase (New England Biolabs M0269S, 10 U) and the use of Exo-Resistant Random primers (Thermo Fisher scientific SO181, 25 μM), dNTPs (0,75 mM each), 50 mM Tris-HCl, 10 mM MgCl2, 10 mM (NH4)2 S04, 4 mM DTT, 0.4 mg/ml BSA, pH 7.5.

| RCA setup | |
|---|---|
| 1 μl DNA (50 ng) | 3 min 95° C. |
| 1 μl primer 1.1 μg | then cool on ice |
| 1 μl 10x buffer | |
| 7 μl H20 | |
| 1 μl 10x buffer | prepare this solution (10 μl) and |
| 0.4 μl BSA 8 μg | add to the sample cooled on ice then, 18 h 30° C. |
| 1.6 μl H2O | 10 min 65° C. |
| 6 μl d-NTP | |
| 1 μl phi29 10U | total Volume of reaction 20 μl |

After RCA, 3 μl of the RCA reaction was used for PCR with BMMF-specific back-to-back primers No (Gag gac gaa tta ata tta caa gtc) and Xo (Gtt ctc gct ttt ctt ggt aa) or Nn (gga tta atg cca atg atc c) and Xn (ctt tgc ctg ttt ctc tcg) with each 10 pmol per 500 reaction together with 8 μl dNTPs, 25 μl buffer GC I, 0.5 μl TAKARA Taq polymerase (Takara RR02AG) with the following PCR setup.

| NoXo/NnXn | | | | | | | | |
|---|---|---|---|---|---|---|---|---|
| 94° C. | 1 min | | | | | 72° C. | 10 min |
| 94° C. | 30 sec | 94° C. | 30 sec | 94° C. | 30 sec | | |
| 64° C. | 1 min | 62° C. | 1 min | 62° C. | 1 min | | |

-continued

| NoXo/NnXn | | | | | |
|---|---|---|---|---|---|
| 72° C. 5 cycles | 2 min | 72° C. 5 cycles | 2 min | 72° C. 30 cycles | 2 min |

If necessary, PCR targets were subjected to an additional cycle of PCR amplification after gel extraction of the PCR targets, whenever the target bands showed inadequate band intensity. After PCR, around 5 ng of DNA was used for cloning into a pCR2.1 TA cloning vector (TA-cloning kit, Invitrogen K203040) according to the manufacturer's protocol followed by sequencing of the PCR insert.

```
                             Sequences

SEQ
ID
NO  SEQUENCE

1  Amino acid sequence of Rep protein encoded by MSBI1.176
    MSDLIVKDNALMNASYNLALVEQRLILLAIIEARETGKGINANDPLTVHASSYINQFN
    VERHTAYQALKDACKDLFARQFSYQEKRERGRINITSRWVSQIGYMDDTATVEIIFAP
    AVVPLITRLEEQFTQYDIEQISGLSSAYAVRMYELLICWRSTGKTPIIELDEFRKRIG
    VLDTEYTRTDNLKMRVIELALKQINEHTDITASYEQHKKGRVITGFSFKFKHKKQNSD
    KTPKNSDSSPRIVKHSQIPTNIVKQPENAKMSDLEHRASRVTGEIMRNRLSDRFKQGD
    ESAIDMMKRIQSEIITDAIADQWESKLEEFGVVF 2  Amino acid sequence of Rep peptide fragment
    EARETGKGINANDPLTVH 3  Amino acid sequence of Rep peptide fragment
    KQINEHTDITASYEQHKKGRT 4  His-Tag (with two neutral stuffer amino acids)
    GAHHHHHH 5  T7-Tag
    MASMTGGQQMG 6  FLAG-Tag
    DYKDDDDK 7  Strep-II-Tag
    WSHPQFEK 8  Amino acid sequence of Rep protein encoded by MSBI2.176
    MSKLVVKDNALMNASYNLDLVEQRLILLAIIEARESGKGINANDPLTVHA
    ESYINQFGVHRVTAYQALKDACDNLFARQFSYQSKSEKGNIQNHRSRWVS
    EIIYIDTEATVKIIFAPAIVPLITRLEEQFTKYDIEQISDLSSAYAIRLY
    ELLICWRSTGKTPIIGLGEFRNRVGVLDSEYHRIAHLKERVIEHSIKQIN
    EHTDITATYEQHKKGRTITGFSFKFKQKKPKQAEIATETPKTATNDPDTT
    KPLTEPQIAKYSMILCKLGSISDLSNFPDYPAFANWIGNILRNPEKADEQ
    IAKRIFTALKTETDYSKKN 9  MSBI.1 specific epitope
    NRLSDRF 10  Amino acid sequence of Rep protein encoded by CMI1.252
    MSDLIVKDNALMNASYNLALVEQRLILLAILEARETGKGINANDPLTVHASSYINQFN
    VERHTAYQALKDACKDLFARQFSYQEKRERGRINITSRWVSQIGYMDDTATVEIIFAP
    AVVPLITRLEEQFTQYDIEQISELSSAYAVRLYELLICWRSTGKTPIIDLTEFRKRLG
    VLDTEYTRTDNLKMRVIELGLKQINEHTDITASYEQHKKGRTITGFSFKFKQKKKTGA
    EMPKNSDSSPHIEKPSQIPANIAKQPENAKKDDLGHRASKITGLIMSNGLADRFKRGD
    ESVIDMMKRIKEEITTDTTADQWENKLEEFGVIFQS 11  Amino acid sequence of Rep protein encoded by CMI2.214
    MSDLIVKDNALMNASYNLDLVEQRLILLAILEARETGKGINANDPLTVHAESYINQFG
    VARQTAYQALKDACKDLFARQFSYQEKRERGRANITSRWVSQIAYIDETATVEVIFAP
    AVVPLITRLEEQFTQYDIEQISGLSSAYAVRLYELLICWRSTGKTPVIELAEFRKRLG
    VLNDEYTRSDNFKKWIIENPIKQINEHTDITASYEQHKKGRTITGFSFKFKQKKKTEP
    ETPKNSDSSQRIEKPSQIPANIVKQPENANLSDLQHRASKITGLIMSNRLSDRFKQGD
    ESIMQMMARIQSEITTDSIADQWQSKLEEFGVVF 12  Amino acid sequence of Rep protein encoded by CMI3.168
    MSDLIVKDNALMNASYNLALVEQRLILLAILEARETGKGINANDPLTVHASSYINQFN
```

| SEQ ID NO | SEQUENCE |
|---|---|
| | VERHTAYQALKDACKDLFARQFSYQEKRERGRANITSRWVSQIAYIDETATVEVIFAP<br>AVVPLITRLEEQFTQYDIEQISGLSSAYAVRLYELLICWRTTGKTPVLDLTEFRKRLG<br>VLDTEYTRTDNLKMRVIEQSLKQINKHTDITASYEQHKKGRTITGFSFKFKQKKKTEP<br>ETPKNNDSGVSKPKTVEIPAEVVKQPKNTNLSDLEKRVRMITGAIAKNNLASRFQHGN<br>ESPLDMMKRIQSEITSDETADLWQNKLESMGVVF |
| 13 | DNA sequence MSBI1 Rep codon-optimized<br>ATGAGCGACCTGATCGTGAAAGACAATGCCCTGATGAACGCCTCCTACAACCTGGCAC<br>TGGTCGAACAGAGACTGATTCTGCTGGCTATCATCGAGGCAAGGGAGACCGGCAAGGG<br>CATCAACGCCAATGACCCCCTGACAGTGCACGCCAGCTCCTACATCAACCAGTTTAAT<br>GTGGAGCGCCACACCGCCTATCAGGCCCTGAAGGACGCCTGCAAGGATCTGTTTGCCC<br>GGCAGTTCAGCTACCAGGAGAAGCGGGAGAGAGGCAGGATCAACATCACAAGCAGATG<br>GGTGTCCCAGATCGGCTATATGGACGATACCGCCACAGTGGAGATCATCTTTGCACCA<br>GCAGTGGTGCCTCTGATCACCAGGCTGGAGGAGCAGTTCACACAGTACGACATCGAGC<br>AGATCTCCGGACTGTCTAGCGCCTACGCCGTGCGCATGTATGAGCTGCTGATCTGTTG<br>GCGGTCTACCGGCAAGACACCTATCATCGAGCTGGATGAGTTCCGCAAGCGGATCGGC<br>GTGCTGGACACCGAGTACACCAGAACAGATAACCTGAAGATGAGAGTGATCGAGCTGG<br>CCCTGAAGCAGATCAATGAGCACACCGATATCACAGCCTCTTATGAGCAGCACAAGAA<br>GGGCCGCGTGATCACCGGCTTCAGCTTTAAGTTCAAGCACAAGAAGCAGAACTCTGAC<br>AAGACACCAAAGAATAGCGATTCCTCTCCCCGGATCGTGAAGCACAGCCAGATCCCTA<br>CCAACATCGTGAAGCAGCCAGAGAATGCCAAGATGTCCGACCTGGAGCACAGGGCATC<br>TAGGGTGACAGGCGAGATCATGAGAAATAGGCTGAGCGATCGGTTCAAGCAGGGCGAC<br>GAGTCCGCCATCGATATGATGAAGAGAATCCAGTCCGAGATCATCACCGACGCCATCG<br>CCGATCAGTGGGAATCTAAACTGGAAGAGTTTGGAGTCGTGTTTGGAGCACATCACCA<br>TCATCATCACTGA |
| 14 | Protein sequence MSBI1 Rep codon-optimized<br>MSDLIVKDNALMNASYNLALVEQRLILLAIIEARETGKGINANDPLTVHASSYINQFN<br>VERHTAYQALKDACKDLFARQFSYQEKRERGRINITSRWVSQIGYMDDTATVEIIFAP<br>AVVPLITRLEEQFTQYDIEQISGLSSAYAVRMYELLICWRSTGKTPIIELDEFRKRIG<br>VLDTEYTRTDNLKMRVIELALKQINEHTDITASYEQHKKGRVITGFSFKFKHKKQNSD<br>KTPKNSDSSPRIVKHSQIPTNIVKQPENAKMSDLEHRASRVTGEIMRNRLSDRFKQGD<br>ESAIDMMKRIQSEIITDAIADQWESKLEEFGVVFGA |
| 15 | DNA sequence MSBI1 Rep wild-type<br>ATGAGCGATTTAATAGTAAAAGATAACGCCCTAATGAATGCTAGTTATAACTTAGCTT<br>TGGTTGAACAGAGGTTAATTCTATTAGCAATCATAGAAGCGAGAGAAACAGGCAAAGG<br>GATTAATGCCAATGATCCTTTAACAGTTCATGCAAGTAGCTATATCAATCAATTTAAC<br>GTAGAAAGGCATACGGCATATCAAGCCCTCAAAGATGCTTGTAAAGACTTGTTTGCCC<br>GTCAATTCAGTTACCAAGAAAAGCGAGAACGAGGACGAATTAATATTACAAGTCGATG<br>GGTTTCGCAAATTGGCTATATGGACGATACAGCAACCGTTGAGATTATTTTTGCCCCT<br>GCGGTTGTTCCTCTGATTACACGGCTAGAGGAACAGTTCACCCAGTACGATATTGAGC<br>AAATTAGCGGTTTATCGAGTGCATATGCTGTTCGTATGTACGAACTGCTGATTTGTTG<br>GCGTAGCACAGGCAAAACACCAATTATTGAGCTAGACGAGTTTAGAAAGCGAATAGGT<br>GTTTTAGATACTGAATACACTAGAACAGATAATTTAAAGATGCGAGTTATTGAATTAG<br>CCCTAAAACAAATCAACGAACATACAGACATCACAGCAAGCTATGAACAACACAAAAA<br>AGGGCGAGTGATTACAGGATTCTCATTCAAGTTTAAGCACAAGAAACAAAACAGCGAT<br>AAAACGCCAAAAAATAGCGATTCTAGCCCACGTATCGTAAAACATAGTCAAATCCCTC<br>CAACATTGTAAAACAGCCTGAAAACGCCAAAATGAGCGATTTAGAACATAGAGCGAGC<br>CGTGTTACAGGGGAAATAATGCGAAATCGTCTGTCAGATCGGTTTAAACAAGGCGATG<br>AATCAGCAATCGACATGATGAAACGTATTCAAAGTGAAATAACCGATGCAATAGC<br>AGACCAGTGGGAAAGCAAACTGGAGGAGTTTGGCGTGGTTTTTTAG |
| 16 | Primer<br>gag gac gaa tta ata tta caa gtc |
| 17 | Primer<br>gtt ctc gct ttt ctt ggt aa |
| 18 | Primer<br>gga tta atg cca atg atc c |
| 19 | Primer<br>ctt tgc ctg ttt ctc tcg |

REFERENCES

Fung, K. Y. C. et al. (2015). "Blood-based protein biomarker panel for the detection of colorectal cancer"., PLOS ONE, Vol. 10, No. 3, p. e0120425.

Funk, M., et al. (2014). "Isolation of protein-associated circular DNA from healthy cattle serum". Genome Announc 2(4).

Giraldo, R., et al. (2011). "RepA-WH1 prionoid: a synthetic amyloid proteinopathy in a minimalist host." Prion 5(2):60-64.

Gunst, K., et al. (2014). "Isolation of bacterial plasmid-related replication-associated cirular DNA from a serum sample of a multiple sclerosis patient." Genome Announc 2(4).

Lamberto, I., et al. (2014). "Mycovirus-like DNA virus sequences from cattle serum and human brain and serum samples from multiple sclerosis patients." Genome Announc 2(4).

Manuelidis L., 2011. "Nuclease resistant circular DNAs co-purify with infectivity in scrapie and CJD". J. Neurovirol. 17:131-145.

Torreira, E., et al. (2015). "Amyloidogenesis of bacterial prionoid RepA-WH1 recatiulates dimer to monomer transitions of RepA in DNA replication initiation." Structure 23(1):183-189.

Whitley, C., et al. (2014). "Novel replication-competent cirulara DNA molecules from healthy cattle serum and milk and multiple sclerosis-affected human brain tissue." Genome Announc 2(4).

zur Hausen, H., Bund, T., de Villiers, E.-M. (2017). "Infectious agents in bovine red meat and milk and their potential role in cancer and other chronic diseases." Curr. Top.Microbiol. Immunol., Volume 407, 83-116.

The invention is further described by the following numbered paragraphs:

1) Use of Bovine Meat and Milk Factor Group 1(BMMF1) Rep Protein as a biomarker for colorectal cancer.

2) The use of paragraph 1 wherein the Rep protein is a MSBI1 genome-encoded Rep protein (MSBI1 Rep), a MSBI2 genome-encoded Rep protein (MSBI2 Rep), a CMI1 genome-encoded Rep protein (CMI1 Rep), a CMI2 genome-encoded Rep protein (CMI2 Rep) or CMI3 genome-encoded Rep protein (CMI3 Rep).

3) A method for providing a diagnosis or predisposition for colorectal cancer (CRC) in a subject, comprising the step of detecting Rep protein in a sample from a subject by anti-Rep antibodies that bind to an epitope comprised by SEQ ID NO: 2 or SEQ ID NO: 3.

4) The method of paragraph 3, wherein the antibody specific for Rep protein binds to an epitope that is within an amino acid sequence selected from the group consisting of amino acids from 1 to 136, from 137 to 229 and from 230 to 324 of SEQ ID NO: 1.

5) The method of paragraph 3 or 4, wherein the sample from a subject is selected from the group consisting of a cancerous colon tissue, peripheral tissue surrounding the cancerous colon tissue, (benign) colon polyps.

6) The method of any of paragraph 3 to 5, wherein additionally CD68 positive cells are detected in the sample by an anti-CD68 antibody.

7) A method for providing a prognostic score on a CRC patient's survival time, comprising the steps of detecting Rep protein in a sample from peritumoral regions of CRC patients by anti-Rep antibodies that bind to an epitope comprised by SEQ ID NO: 2 or SEQ ID NO: 3, determining for each antibody the percentage of stained cells and intensity proposing a immunohistological score which serves as general indicator of CRC-specific patient survival time.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. A method for providing a diagnosis or predisposition for colorectal cancer (CRC) in a subject, comprising:
   obtaining a sample from a subject;
   detecting whether a Bovine Meat and Milk Factor Group 1 (BMMF1) Rep Protein is present in the sample by contacting the sample with one or more antibodies selected from the group consisting of Ab 1-5 (DSM ACC3327), Ab 5-2 (DSM ACC3328) and Ab 3-6 (DSM ACC3329) and detecting binding between BMMF1 and said one or more antibodies; and
   providing a diagnosis or predisposition for CRC to the subject when the presence of BMMF1 in the sample is detected.

2. The method of claim 1, wherein the sample from the subject is selected from the group consisting of a cancerous colon tissue, peripheral tissue surrounding the cancerous colon tissue and benign colon polyps.

3. The method of claim 1, wherein additionally CD68 positive cells are detected in the sample by an anti-CD68 antibody.

4. A method for providing a prognostic score on a CRC patient's survival time, comprising:
   a) obtaining a sample from peritumoral regions of CRC patients;
   b) contacting the sample with one or more antibodies selected from the group consisting of Ab 1-5 (DSM ACC3327), Ab 5-2 (DSM ACC3328) and Ab 3-6 (DSM ACC3329),
   c) staining the sample to visualize binding between Rep protein and the one or more antibodies;
   d) detecting Rep protein in the stained sample by observing the visualized binding;
   e) quantifying the detected Rep protein by:
      i) determining for each antibody the percentage of stained cells, and
      ii) measuring the staining intensity;
   f) calculating an immunohistological score based on the quantified Rep protein; and
   g) correlating the calculated immunohistological score to a CRC-specific patient's survival time.

* * * * *

SEQUENCE LISTING

```
<160> NUMBER OF SEQ ID NOS: 19

<210> SEQ ID NO 1
<211> LENGTH: 324
<212> TYPE: PRT
<213> ORGANISM: artificial sequence
<220> FEATURE:
<223> OTHER INFORMATION: MSBI1 Rep protein

<400> SEQUENCE: 1

Met Ser Asp Leu Ile Val Lys Asp Asn Ala Leu Met Asn Ala Ser Tyr
1               5                   10                  15

Asn Leu Ala Leu Val Glu Gln Arg Leu Ile Leu Leu Ala Ile Ile Glu
            20                  25                  30

Ala Arg Glu Thr Gly Lys Gly Ile Asn Ala Asn Asp Pro Leu Thr Val
        35                  40                  45

His Ala Ser Ser Tyr Ile Asn Gln Phe Asn Val Glu Arg His Thr Ala
    50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ile Asn Ile Thr Ser Arg
                85                  90                  95

Trp Val Ser Gln Ile Gly Tyr Met Asp Asp Thr Ala Thr Val Glu Ile
```

```
                  100                 105                 110
Ile Phe Ala Pro Ala Val Val Pro Leu Ile Thr Arg Leu Glu Glu Gln
            115                 120                 125

Phe Thr Gln Tyr Asp Ile Glu Gln Ile Ser Gly Leu Ser Ser Ala Tyr
            130                 135                 140

Ala Val Arg Met Tyr Glu Leu Leu Ile Cys Trp Arg Ser Thr Gly Lys
145                 150                 155                 160

Thr Pro Ile Ile Glu Leu Asp Glu Phe Arg Lys Arg Ile Gly Val Leu
                165                 170                 175

Asp Thr Glu Tyr Thr Arg Thr Asp Asn Leu Lys Met Arg Val Ile Glu
            180                 185                 190

Leu Ala Leu Lys Gln Ile Asn Glu His Thr Asp Ile Thr Ala Ser Tyr
            195                 200                 205

Glu Gln His Lys Lys Gly Arg Val Ile Thr Gly Phe Ser Phe Lys Phe
            210                 215                 220

Lys His Lys Lys Gln Asn Ser Asp Lys Thr Pro Lys Asn Ser Asp Ser
225                 230                 235                 240

Ser Pro Arg Ile Val Lys His Ser Gln Ile Pro Thr Asn Ile Val Lys
                245                 250                 255

Gln Pro Glu Asn Ala Lys Met Ser Asp Leu Glu His Arg Ala Ser Arg
            260                 265                 270

Val Thr Gly Glu Ile Met Arg Asn Arg Leu Ser Asp Arg Phe Lys Gln
            275                 280                 285

Gly Asp Glu Ser Ala Ile Asp Met Met Lys Arg Ile Gln Ser Glu Ile
            290                 295                 300

Ile Thr Asp Ala Ile Ala Asp Gln Trp Glu Ser Lys Leu Glu Glu Phe
305                 310                 315                 320

Gly Val Val Phe

<210> SEQ ID NO 2
<211> LENGTH: 18
<212> TYPE: PRT
<213> ORGANISM: artificial sequence
<220> FEATURE:
<223> OTHER INFORMATION: Rep peptide

<400> SEQUENCE: 2

Glu Ala Arg Glu Thr Gly Lys Gly Ile Asn Ala Asn Asp Pro Leu Thr
1               5                   10                  15

Val His

<210> SEQ ID NO 3
<211> LENGTH: 20
<212> TYPE: PRT
<213> ORGANISM: artificial sequence
<220> FEATURE:
<223> OTHER INFORMATION: Rep peptide

<400> SEQUENCE: 3

Lys Gln Ile Asn Glu His Thr Asp Ile Thr Ala Ser Tyr Glu His Lys
1               5                   10                  15

Lys Gly Arg Thr
            20

<210> SEQ ID NO 4
<211> LENGTH: 8
<212> TYPE: PRT
<213> ORGANISM: artificial sequence
```

```
<220> FEATURE:
<223> OTHER INFORMATION: His tag

<400> SEQUENCE: 4

Gly Ala His His His His His His
1               5

<210> SEQ ID NO 5
<211> LENGTH: 11
<212> TYPE: PRT
<213> ORGANISM: artificial sequence
<220> FEATURE:
<223> OTHER INFORMATION: T7 tag

<400> SEQUENCE: 5

Met Ala Ser Met Thr Gly Gly Gln Gln Met Gly
1               5                   10

<210> SEQ ID NO 6
<211> LENGTH: 8
<212> TYPE: PRT
<213> ORGANISM: artificial sequence
<220> FEATURE:
<223> OTHER INFORMATION: FLAG tag

<400> SEQUENCE: 6

Asp Tyr Lys Asp Asp Asp Asp Lys
1               5

<210> SEQ ID NO 7
<211> LENGTH: 8
<212> TYPE: PRT
<213> ORGANISM: artificial sequence
<220> FEATURE:
<223> OTHER INFORMATION: Trep II tag

<400> SEQUENCE: 7

Trp Ser His Pro Gln Phe Glu Lys
1               5

<210> SEQ ID NO 8
<211> LENGTH: 319
<212> TYPE: PRT
<213> ORGANISM: artificial sequence
<220> FEATURE:
<223> OTHER INFORMATION: MSBI2.176

<400> SEQUENCE: 8
```

Met Ser Lys Leu Val Val Lys Asp Asn Ala Leu Met Asn Ala Ser Tyr
1               5                   10                  15

Asn Leu Asp Leu Val Glu Gln Arg Leu Ile Leu Ala Ile Ile Glu
            20                  25                  30

Ala Arg Glu Ser Gly Lys Gly Ile Asn Ala Asn Asp Pro Leu Thr Val
        35                  40                  45

His Ala Glu Ser Tyr Ile Asn Gln Phe Gly Val His Arg Val Thr Ala
    50                  55                  60

Tyr Gln Ala Leu Lys Asp Ala Cys Asp Asn Leu Phe Ala Arg Gln Phe
65                  70                  75                  80

Ser Tyr Gln Ser Lys Ser Glu Lys Gly Asn Ile Gln Asn His Arg Ser
                85                  90                  95

Arg Trp Val Ser Glu Ile Ile Tyr Ile Asp Thr Glu Ala Thr Val Lys
                100                 105                 110

Ile Ile Phe Ala Pro Ala Ile Val Pro Leu Ile Thr Arg Leu Glu Glu

```
                115                 120                 125
Gln Phe Thr Lys Tyr Asp Ile Glu Gln Ile Ser Asp Leu Ser Ser Ala
    130                 135                 140

Tyr Ala Ile Arg Leu Tyr Glu Leu Leu Ile Cys Trp Arg Ser Thr Gly
145                 150                 155                 160

Lys Thr Pro Ile Ile Gly Leu Gly Glu Phe Arg Asn Arg Val Gly Val
                165                 170                 175

Leu Asp Ser Glu Tyr His Arg Ile Ala His Leu Lys Glu Arg Val Ile
            180                 185                 190

Glu His Ser Ile Lys Gln Ile Asn Glu His Thr Asp Ile Thr Ala Thr
        195                 200                 205

Tyr Glu Gln His Lys Lys Gly Arg Thr Ile Thr Gly Phe Ser Phe Lys
    210                 215                 220

Phe Lys Gln Lys Pro Lys Gln Ala Glu Ile Ala Thr Glu Thr Pro
225                 230                 235                 240

Lys Thr Ala Thr Asn Asp Pro Asp Thr Thr Lys Pro Leu Thr Glu Pro
                245                 250                 255

Gln Ile Ala Lys Tyr Ser Met Ile Leu Cys Lys Leu Gly Ser Ile Ser
            260                 265                 270

Asp Leu Ser Asn Phe Pro Asp Tyr Pro Ala Phe Ala Asn Trp Ile Gly
        275                 280                 285

Asn Ile Leu Arg Asn Pro Glu Lys Ala Asp Glu Gln Ile Ala Lys Arg
    290                 295                 300

Ile Phe Thr Ala Leu Lys Thr Glu Thr Asp Tyr Ser Lys Lys Asn
305                 310                 315

<210> SEQ ID NO 9
<211> LENGTH: 7
<212> TYPE: PRT
<213> ORGANISM: artificial sequence
<220> FEATURE:
<223> OTHER INFORMATION: MSBI1 epitope

<400> SEQUENCE: 9

Asn Arg Leu Ser Asp Arg Phe
1               5

<210> SEQ ID NO 10
<211> LENGTH: 326
<212> TYPE: PRT
<213> ORGANISM: Artificial Sequence
<220> FEATURE:
<223> OTHER INFORMATION: CMI1.252

<400> SEQUENCE: 10

Met Ser Asp Leu Ile Val Lys Asp Asn Ala Leu Met Asn Ala Ser Tyr
1               5                   10                  15

Asn Leu Ala Leu Val Glu Gln Arg Leu Ile Leu Leu Ala Ile Leu Glu
            20                  25                  30

Ala Arg Glu Thr Gly Lys Gly Ile Asn Ala Asn Asp Pro Leu Thr Val
        35                  40                  45

His Ala Ser Ser Tyr Ile Asn Gln Phe Asn Val Glu Arg His Thr Ala
    50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ile Asn Ile Thr Ser Arg
                85                  90                  95
```

Trp Val Ser Gln Ile Gly Tyr Met Asp Asp Thr Ala Thr Val Glu Ile
100                 105                 110

Ile Phe Ala Pro Ala Val Val Pro Leu Ile Thr Arg Leu Glu Glu Gln
            115                 120                 125

Phe Thr Gln Tyr Asp Ile Glu Gln Ile Ser Glu Leu Ser Ser Ala Tyr
130                 135                 140

Ala Val Arg Leu Tyr Glu Leu Leu Ile Cys Trp Arg Ser Thr Gly Lys
145                 150                 155                 160

Thr Pro Ile Ile Asp Leu Thr Glu Phe Arg Lys Arg Leu Gly Val Leu
                165                 170                 175

Asp Thr Glu Tyr Thr Arg Thr Asp Asn Leu Lys Met Arg Val Ile Glu
            180                 185                 190

Leu Gly Leu Lys Gln Ile Asn Glu His Thr Asp Ile Thr Ala Ser Tyr
        195                 200                 205

Glu Gln His Lys Lys Gly Arg Thr Ile Thr Gly Phe Ser Phe Lys Phe
210                 215                 220

Lys Gln Lys Lys Lys Thr Gly Ala Glu Met Pro Lys Asn Ser Asp Ser
225                 230                 235                 240

Ser Pro His Ile Glu Lys Pro Ser Gln Ile Pro Ala Asn Ile Ala Lys
                245                 250                 255

Gln Pro Glu Asn Ala Lys Lys Asp Asp Leu Gly His Arg Ala Ser Lys
            260                 265                 270

Ile Thr Gly Leu Ile Met Ser Asn Gly Leu Ala Asp Arg Phe Lys Arg
        275                 280                 285

Gly Asp Glu Ser Val Ile Asp Met Met Lys Arg Ile Lys Glu Glu Ile
290                 295                 300

Thr Thr Asp Thr Thr Ala Asp Gln Trp Glu Asn Lys Leu Glu Glu Phe
305                 310                 315                 320

Gly Val Ile Phe Gln Ser
                325

<210> SEQ ID NO 11
<211> LENGTH: 324
<212> TYPE: PRT
<213> ORGANISM: Artificial Sequence
<220> FEATURE:
<223> OTHER INFORMATION: CMI2.214

<400> SEQUENCE: 11

Met Ser Asp Leu Ile Val Lys Asp Asn Ala Leu Met Asn Ala Ser Tyr
1               5                   10                  15

Asn Leu Asp Leu Val Glu Gln Arg Leu Ile Leu Ala Ile Leu Glu
            20                  25                  30

Ala Arg Glu Thr Gly Lys Gly Ile Asn Ala Asn Asp Pro Leu Thr Val
            35                  40                  45

His Ala Glu Ser Tyr Ile Asn Gln Phe Gly Val Ala Arg Gln Thr Ala
        50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ala Asn Ile Thr Ser Arg
                85                  90                  95

Trp Val Ser Gln Ile Ala Tyr Ile Asp Glu Thr Ala Thr Val Glu Val
            100                 105                 110

Ile Phe Ala Pro Ala Val Val Pro Leu Ile Thr Arg Leu Glu Glu Gln
        115                 120                 125

Phe Thr Gln Tyr Asp Ile Glu Gln Ile Ser Gly Leu Ser Ser Ala Tyr
    130                 135                 140

Ala Val Arg Leu Tyr Glu Leu Leu Ile Cys Trp Arg Ser Thr Gly Lys
145                 150                 155                 160

Thr Pro Val Ile Glu Leu Ala Glu Phe Arg Lys Arg Leu Gly Val Leu
                165                 170                 175

Asn Asp Glu Tyr Thr Arg Ser Asp Asn Phe Lys Lys Trp Ile Ile Glu
                180                 185                 190

Asn Pro Ile Lys Gln Ile Asn Glu His Thr Asp Ile Thr Ala Ser Tyr
                195                 200                 205

Glu Gln His Lys Lys Gly Arg Thr Ile Thr Gly Phe Ser Phe Lys Phe
    210                 215                 220

Lys Gln Lys Lys Thr Glu Pro Glu Thr Pro Lys Asn Ser Asp Ser
225                 230                 235                 240

Ser Gln Arg Ile Glu Lys Pro Ser Gln Ile Pro Ala Asn Ile Val Lys
                245                 250                 255

Gln Pro Glu Asn Ala Asn Leu Ser Asp Leu Gln His Arg Ala Ser Lys
    260                 265                 270

Ile Thr Gly Leu Ile Met Ser Asn Arg Leu Ser Asp Arg Phe Lys Gln
    275                 280                 285

Gly Asp Glu Ser Ile Met Gln Met Met Ala Arg Ile Gln Ser Glu Ile
    290                 295                 300

Thr Thr Asp Ser Ile Ala Asp Gln Trp Gln Ser Lys Leu Glu Glu Phe
305                 310                 315                 320

Gly Val Val Phe

<210> SEQ ID NO 12
<211> LENGTH: 324
<212> TYPE: PRT
<213> ORGANISM: Artificial Sequence
<220> FEATURE:
<223> OTHER INFORMATION: CMI3.168

<400> SEQUENCE: 12

Met Ser Asp Leu Ile Val Lys Asp Asn Ala Leu Met Asn Ala Ser Tyr
1               5                   10                  15

Asn Leu Ala Leu Val Glu Gln Arg Leu Ile Leu Ala Ile Leu Glu
            20                  25                  30

Ala Arg Glu Thr Gly Lys Gly Ile Asn Ala Asn Asp Pro Leu Thr Val
                35                  40                  45

His Ala Ser Ser Tyr Ile Asn Gln Phe Asn Val Glu Arg His Thr Ala
    50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ala Asn Ile Thr Ser Arg
                85                  90                  95

Trp Val Ser Gln Ile Ala Tyr Ile Asp Glu Thr Ala Thr Val Glu Val
                100                 105                 110

Ile Phe Ala Pro Ala Val Val Pro Leu Ile Thr Arg Leu Glu Glu Gln
            115                 120                 125

Phe Thr Gln Tyr Asp Ile Glu Gln Ile Ser Gly Leu Ser Ser Ala Tyr
    130                 135                 140

Ala Val Arg Leu Tyr Glu Leu Leu Ile Cys Trp Arg Thr Thr Gly Lys
145                 150                 155                 160

Thr Pro Val Leu Asp Leu Thr Glu Phe Arg Lys Arg Leu Gly Val Leu

```
                165                 170                 175
Asp Thr Glu Tyr Thr Arg Thr Asp Asn Leu Lys Met Arg Val Ile Glu
            180                 185                 190

Gln Ser Leu Lys Gln Ile Asn Lys His Thr Asp Ile Thr Ala Ser Tyr
        195                 200                 205

Glu Gln His Lys Lys Gly Arg Thr Ile Thr Gly Phe Ser Phe Lys Phe
    210                 215                 220

Lys Gln Lys Lys Thr Glu Pro Glu Thr Pro Lys Asn Asn Asp Ser
225                 230                 235                 240

Gly Val Ser Lys Pro Lys Thr Val Glu Ile Pro Ala Glu Val Val Lys
                245                 250                 255

Gln Pro Lys Asn Thr Asn Leu Ser Asp Leu Glu Lys Arg Val Arg Met
            260                 265                 270

Ile Thr Gly Ala Ile Ala Lys Asn Asn Leu Ala Ser Arg Phe Gln His
        275                 280                 285

Gly Asn Glu Ser Pro Leu Asp Met Met Lys Arg Ile Gln Ser Glu Ile
    290                 295                 300

Thr Ser Asp Glu Thr Ala Asp Leu Trp Gln Asn Lys Leu Glu Ser Met
305                 310                 315                 320

Gly Val Val Phe

<210> SEQ ID NO 13
<211> LENGTH: 999
<212> TYPE: DNA
<213> ORGANISM: artificial sequence
<220> FEATURE:
<223> OTHER INFORMATION: codon-optimized MSBI1

<400> SEQUENCE: 13
atgagcgacc tgatcgtgaa agacaatgcc ctgatgaacg cctcctacaa cctggcactg      60
gtcgaacaga gactgattct gctggctatc atcgaggcaa gggagaccgg caagggcatc     120
aacgccaatg accccctgac agtgcacgcc agctcctaca tcaaccagtt taatgtggag     180
cgccacaccg cctatcaggc cctgaaggac gcctgcaagg atctgtttgc ccggcagttc     240
agctaccagg agaagcggga gagaggcagg atcaacatca caagcagatg ggtgtcccag     300
atcggctata tggacgatac cgccacagtg gagatcatct ttgcaccagc agtggtgcct     360
ctgatcacca ggctggagga gcagttcaca cagtacgaca tcgagcagat ctccggactg     420
tctagcgcct acgccgtgcg catgtatgag ctgctgatct gttggcggtc taccggcaag     480
acacctatca tcgagctgga tgagttccgc aagcggatcg gcgtgctgga caccgagtac     540
accagaacag ataacctgaa gatgagagtg atcgagctgg ccctgaagca gatcaatgag     600
cacaccgata tcacagcctc ttatgagcag cacaagaagg gccgcgtgat caccggcttc     660
agctttaagt tcaagcacaa gaagcagaac tctgacaaga caccaaagaa tagcgattcc     720
tctcccggga tcgtgaagca cagccagatc cctaccaaca tcgtgaagca gccagagaat     780
gccaagatgt ccgacctgga gcacagggca tctagggtga caggcgagat catgagaaat     840
aggctgagcg atcggttcaa gcagggcgac gagtccgcca tcgatatgat gaagagaatc     900
cagtccgaga tcatcaccga cgccatcgcc gatcagtggg aatctaaact ggaagagttt     960
ggagtcgtgt ttggagcaca tcaccatcat catcactga                             999

<210> SEQ ID NO 14
<211> LENGTH: 326
<212> TYPE: PRT
```

<213> ORGANISM: artificial sequence
<220> FEATURE:
<223> OTHER INFORMATION: MSBI1 protein

<400> SEQUENCE: 14

Met Ser Asp Leu Ile Val Lys Asp Asn Ala Leu Met Asn Ala Ser Tyr
1               5                   10                  15

Asn Leu Ala Leu Val Glu Gln Arg Leu Ile Leu Leu Ala Ile Ile Glu
            20                  25                  30

Ala Arg Glu Thr Gly Lys Gly Ile Asn Ala Asn Asp Pro Leu Thr Val
        35                  40                  45

His Ala Ser Ser Tyr Ile Asn Gln Phe Asn Val Glu Arg His Thr Ala
    50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ile Asn Ile Thr Ser Arg
                85                  90                  95

Trp Val Ser Gln Ile Gly Tyr Met Asp Asp Thr Ala Thr Val Glu Ile
            100                 105                 110

Ile Phe Ala Pro Ala Val Val Pro Leu Ile Thr Arg Leu Glu Glu Gln
        115                 120                 125

Phe Thr Gln Tyr Asp Ile Glu Gln Ile Ser Gly Leu Ser Ser Ala Tyr
    130                 135                 140

Ala Val Arg Met Tyr Glu Leu Leu Ile Cys Trp Arg Ser Thr Gly Lys
145                 150                 155                 160

Thr Pro Ile Ile Glu Leu Asp Glu Phe Arg Lys Arg Ile Gly Val Leu
                165                 170                 175

Asp Thr Glu Tyr Thr Arg Thr Asp Asn Leu Lys Met Arg Val Ile Glu
            180                 185                 190

Leu Ala Leu Lys Gln Ile Asn Glu His Thr Asp Ile Thr Ala Ser Tyr
        195                 200                 205

Glu Gln His Lys Lys Gly Arg Val Ile Thr Gly Phe Ser Phe Lys Phe
    210                 215                 220

Lys His Lys Lys Gln Asn Ser Asp Lys Thr Pro Lys Asn Ser Asp Ser
225                 230                 235                 240

Ser Pro Arg Ile Val Lys His Ser Gln Ile Pro Thr Asn Ile Val Lys
                245                 250                 255

Gln Pro Glu Asn Ala Lys Met Ser Asp Leu Glu His Arg Ala Ser Arg
            260                 265                 270

Val Thr Gly Glu Ile Met Arg Asn Arg Leu Ser Asp Arg Phe Lys Gln
        275                 280                 285

Gly Asp Glu Ser Ala Ile Asp Met Met Lys Arg Ile Gln Ser Glu Ile
    290                 295                 300

Ile Thr Asp Ala Ile Ala Asp Gln Trp Glu Ser Lys Leu Glu Glu Phe
305                 310                 315                 320

Gly Val Val Phe Gly Ala
                325

<210> SEQ ID NO 15
<211> LENGTH: 974
<212> TYPE: DNA
<213> ORGANISM: artificial sequence
<220> FEATURE:
<223> OTHER INFORMATION: MSBI1 wild type

<400> SEQUENCE: 15

```
atgagcgatt taatagtaaa agataacgcc ctaatgaatg ctagttataa cttagctttg      60
gttgaacaga ggttaattct attagcaatc atagaagcga gagaaacagg caagggatt      120 aatgccaatg atcctttaac agttcatgca agtagctata tcaatcaatt taacgtagaa     180
aggcatacgg catatcaagc cctcaaagat gcttgtaaag acttgtttgc ccgtcaattc     240
agttaccaag aaaagcgaga acgaggacga attaatatta caagtcgatg ggtttcgcaa     300
attggctata tggacgatac agcaaccgtt gagattattt ttgcccctgc ggttgttcct     360
ctgattacac ggctagagga acagttcacc cagtacgata ttgagcaaat tagcggttta     420
tcgagtgcat atgctgttcg tatgtacgaa ctgctgattt gttggcgtag cacaggcaaa     480
acaccaatta ttgagctaga cgagtttaga aagcgaatag gtgttttaga tactgaatac     540
actagaacag ataatttaaa gatgcgagtt attgaattag ccctaaaaca aatcaacgaa     600
catacagaca tcacagcaag ctatgaacaa cacaaaaaag ggcgagtgat tacaggattc     660
tcattcaagt ttaagcacaa gaaacaaaac agcgataaaa cgccaaaaaa tagcgattct     720
agcccacgta tcgtaaaaca tagtcaaatc cctccaacat tgtaaaacag cctgaaaacg     780
ccaaaatgag cgatttagaa catagagcga gccgtgttac aggggaaata atgcgaaatc     840
gtctgtcaga tcggtttaaa caaggcgatg aatcagcaat cgacatgatg aaacgtattc     900
aaagtgaaat aataaccgat gcaatagcag accagtggga aagcaaactg gaggagtttg     960
gcgtggtttt ttag                                                       974

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
gaggacgaat taatattaca agtc                                             24

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
gttctcgctt ttcttggtaa                                                  20

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
ggattaatgc caatgatcc                                                   19

<210> SEQ ID NO 19
<211> LENGTH: 18
<212> TYPE: DNA
<213> ORGANISM: Artificial Sequence
```

```
<220> FEATURE:
<223> OTHER INFORMATION: primer

<400> SEQUENCE: 19
ctttgcctgt ttctctcg                                                      18
```